(12) United States Patent
Díaz Rebolledo et al.

(10) Patent No.: US 10,220,067 B2
(45) Date of Patent: Mar. 5, 2019

(54) **EXTRACTS OF *CYCLANTHERA PEDATA* AND FORMULATIONS AND USES THEREOF**

(71) Applicants: Alejandro Mario Díaz Rebolledo, Barranquilla (CO); Carlos Perez Rebolledo, Barranquilla (CO)

(72) Inventors: Alejandro Mario Díaz Rebolledo, Barranquilla (CO); Carlos Perez Rebolledo, Barranquilla (CO)

(73) Assignee: PROCAPS SA, Barranquilla (CO)

( * ) Notice: Subject to any disclaimer, the term of this patent is extended or adjusted under 35 U.S.C. 154(b) by 0 days.

(21) Appl. No.: 15/361,215

(22) Filed: Nov. 25, 2016

(65) Prior Publication Data

US 2017/0071995 A1 Mar. 16, 2017

Related U.S. Application Data

(63) Continuation-in-part of application No. 15/096,938, filed on Apr. 12, 2016, which is a continuation of application No. 14/839,977, filed on Aug. 29, 2015.

(60) Provisional application No. 62/043,484, filed on Aug. 29, 2014.

(51) Int. Cl.
| | |
|---|---|
| *A61K 36/42* | (2006.01) |
| *A61K 35/60* | (2006.01) |
| *A61K 35/612* | (2015.01) |
| *A61K 9/00* | (2006.01) |
| *A61K 9/16* | (2006.01) |
| *A61K 9/48* | (2006.01) |
| *A61P 1/16* | (2006.01) |
| *A61K 45/06* | (2006.01) |

(52) U.S. Cl.
CPC ............ *A61K 36/42* (2013.01); *A61K 9/0053* (2013.01); *A61K 9/1664* (2013.01); *A61K 9/4875* (2013.01); *A61K 35/60* (2013.01); *A61K 35/612* (2013.01); *A61P 1/16* (2018.01); *A61K 45/06* (2013.01); *A61K 2236/10* (2013.01); *A61K 2236/30* (2013.01); *A61K 2236/50* (2013.01)

(58) Field of Classification Search
None
See application file for complete search history.

(56) References Cited

U.S. PATENT DOCUMENTS

2010/0136064 A1* 6/2010 Shatkina .............. A61K 8/0212
424/400

OTHER PUBLICATIONS

Cavallini et al. (2013) Intern. J. Environ. Anal. Chem. vol. 93, No. 8, 906-918. (Year: 2013).*
Rivas et al. (2013) Food Nutr. Sci. vol. 04, Issue 08 pp. 55-61 (Year: 2013).*
Alvaro et al. (2009) Journal of Food Engineering 95: 11-15. (Year: 2009).*
Carbone et al. (2004) J. Pharma. Biomed. Anal. 34: 295-304. (Year: 2004).*
Website Document entitled: "Tropical Plant Database: Caigua" (available at http://www.rain-tree.com/caigua.htm#.WniftWaWxaQ). Dated 2006. Downloaded Feb. 5, 2018. (Year: 2006).*
Montoro et al. (2001) J. Agric. Food Chem. 49: 5156-5160. (Year: 2001).*
Ranilla et al. (2010) Bioresource Technology 101: 4676-4689. (Year: 2010).*
Raskin et al. (2004) Current Pharmaceutical Design, 10, 3419-3429. (Year: 2004).*
Revilla et al. (1998) J. Agric. Food Chem. 46: 4592-4597. (Year: 1998).*
Tommasi et al. (1999) J. Agric. Food Chem. 47: 4512-4519. (Year: 1999).*

* cited by examiner

*Primary Examiner* — Christopher R Tate
*Assistant Examiner* — Russell G Fiebig
(74) *Attorney, Agent, or Firm* — Isaac Angres

(57) ABSTRACT

The invention provides a method for extracting active therapeutic components from plant materials of the *Cyclanthera pedata* plant which comprises immersing said plant material containing active components and selected from the group consisting of fruits, flowers, leaves, stems, twigs, bark, wood, buds, seeds, roots, and pods in a solvent for a period of time of about 30 minutes to about 10 hours to achieve transfer of active components from the plant material to the solvent, separating the solvent containing active components from the plant material, and evaporating or distilling the solvent to produce a concentrated fraction containing active components. The invention further includes compositions and therapeutic formulations of such extracts to treat hypercholesterolemia and other high lipid related diseases.

1 Claim, 5 Drawing Sheets

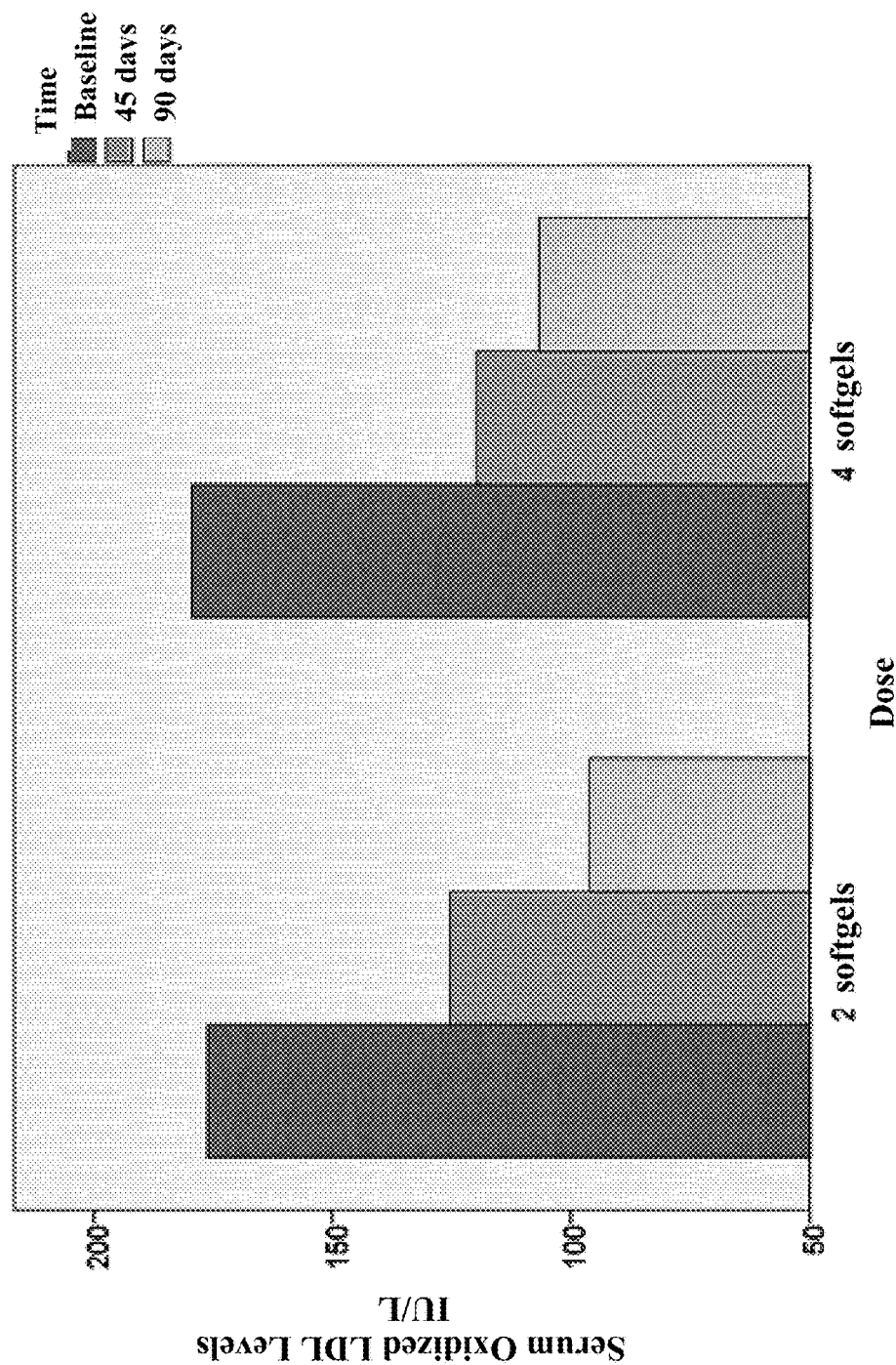

EXTRACTS OF *CYCLANTHERA PEDATA* AND FORMULATIONS AND USES THEREOF

This application is a continuation-in-part of U.S. application Ser. No. 15/096,938 entitled "Extracts Of *Cyclanthera pedata* And Formulations And Uses Thereof" filed Apr. 12, 2016; which application is a continuation of U.S. application Ser. No. 14/839,977 entitled "Extracts Of *Cyclanthera pedata* And Formulations And Uses Thereof" filed on Aug. 29, 2015; the entire contents of which are incorporated by reference herein. This application also claims the priority benefit under 35 U.S.C. section 119 of U.S. Provisional Patent Application No. 62/043,484 entitled "Extracts Of *Cyclanthera pedata* And Formulations And Uses Thereof" filed on Aug. 29, 2014; which is in its entirety herein incorporated by reference.

FIELD OF THE INVENTION

The present invention provides a composition obtained by polar organic solvent extraction of plant material derived from the *Cyclanthera pedata* plant which is an atherosclerosis preventative agent. The present invention further provides a food, a dietary supplement and a pharmaceutical composition containing the composition, as well as a method of preventing an atherosclerotic disease.

The present invention relates to plant extracts and the use of plant extracts for medicinal purposes. More specifically, the present invention relates to plant extracts of the *Cyclanthera* plant and their use for lowering cellular cholesterol and cholesteryl ester concentration. This invention relates to the preparation by solvent extraction from the plant *Cyclanthera* and preferably from the species *Cyclanthera pedata* which possesses biological activity, and the use of such extracts for the treatment of hypercholesterolemia and atherosclerosis.

The present invention also relates to lipid reducing agents and more specifically to those agents which reduce the amount of lipids in serum and in the liver, said agents comprising substances solvent-extracted from *Cyclanthera pedata* plants.

The instant invention also relates to natural extracts in combination with other therapeutic agents or natural materials having therapeutic activity for treating hypercholesterolemia. The invention further relates to a composition that contains an extract from the *Cyclanthera pedata* plant which help individuals support healthy cholesterol levels.

The present invention relates to pharmaceutical composition useful for the treatment of hyperlipidemia that include extracts from the *Cyclanthera pedata* plant.

BACKGROUND OF THE INVENTION

Coronary heart disease continues to be a leading cause of morbidity and mortality in developed countries. It is rapidly assuming similar trends in developing countries also. The heart operates similar to a pulsatile pump, in that blood enters the arteries intermittently with each heart beat, causing pressure pulses in the arterial system. In a healthy circulatory system, the pressure at the height of a pulse (systolic pressure is approximately 120 mm Hg and the pressure at the lowest point of the pulse (diastolic pressure) is approximately 80 mm Hg. The difference between these two pressures, 40 mm Hg, is termed the pulse pressure (Guyton and Hall, TEXTBOOK OF MEDICAL PHYSIOLOGY 221 (6th ed., W. B. Saunders Company, 1956) (1981)). Stroke volume output of the heart and compliance of the arterial system are the two most important factors in pulse pressure.

Atherosclerosis, which is the principal cause of death in Western countries, decreases arterial compliance by depositing calcified plaques on arterial walls, thereby reducing the elasticity of arterial walls. When this occurs, systolic pressure increases greatly, while diastolic pressure, the pressure that causes blood to be transferred from the arteries to the veins, is decreased greatly. Thus, blood becomes backed-up in the system, due to the inability of blood to flow through the arteries efficiently, as well as, the inability of blood to flow back to the heart. One key process of artherosclerosis is the accumulation of lipids resulting in distribution of atheromatous plaque. As plaque accumulates in the inner artery wall, the restricted artery is weakened, bulging with cholesterol and toxic deposits. Eventually, the plaque blocks the arteries and interrupts blood flow to the organs they supply. Thus, hyperlipidemia (elevated levels of lipids), and specifically, hypercholesterolemia (elevated levels of cholesterol) are major risk factors for atherosclerosis.

It is known that there are three forms of cholesterol: very low-density lipoprotein (VLDL), low-density lipoprotein (LDL) and high-density lipoprotein (HDL). Arterial wall cholesterol, and therefore atherosclerotic plaque, consists almost exclusively of LDL. Overwhelming evidence shows that LDL cholesterol becomes harmful only in its oxidized form known as oxysterol. HDL on the other hand, has been found to be inversely associated with coronary artery disease. It has been determined that for every 1 percent increase in the HDL cholesterol level, the risk of having a coronary event is decreased 3 percent. There are two generally accepted approaches to preventing CVD. The first is to lower LDL cholesterol levels and/or increase HDL cholesterol levels and the other is to reduce levels of oxidized cholesterol.

Several studies have demonstrated that lowering LDL cholesterol levels reduces death from heart disease. The Scandinavian Simvastatin Survival Study followed 4,444 men and women with a history of angina or heart attack over 5.4 years (344 LANCET 1383-389 (1994)). The study showed that simvastatin, a cholesterol lowering drug, was effective at lowering LDL and thus decreasing deaths and the need for bypass and angioplasty surgery. The Cholesterol and Recurrent Events Trial demonstrated that pravastatin, another cholesterol lowering drug, was effective at lowering LDL cholesterol by 28%, heart attacks by 25%, and strokes by 28%. The study involved 4,158 men and women with a recent history of heart attack (Sacks et al., 335 N. ENGL. J. MED. 1001-1009 (1996)).

A host of LDL cholesterol lowering drugs is currently on the market. The most widely used lipid-lowering drugs include simvastatin, pravastatin, lovastatin, fluvastatin, atorvastatin, and cerivastatin, which make up the group of HMG-CoA reductase inhibitors known as statins. The statins inhibit one of the enzymes responsible for manufacturing VLDL in the liver (HMG-CoA reductase). In response to a lower level of VLDL, the liver removes LDL from the bloodstream to compensate for the loss of VLDL, thereby reducing LDL cholesterol levels in the blood. Statins have also been found to increase HDL levels in some patients. Although effective, the statins are associated with several side effects including reversible liver enzyme elevations, gastrointestinal upset, headache, dizziness, mild skin rashes, muscle pain and muscle inflammation at high dosages. Moreover, serious liver toxicity is possible. Side effects notwithstanding, recent coronary angiography trials have revealed that if LDL cholesterol can be lowered below 100 mg/dl using cholesterol lowering drugs, atherosclerosis progression is arrested in only 50% to 60% of patients. Alternative cholesterol lowering drugs include: (1) fibrates, gemfibrozil and clofibrate, which activate the enzyme lipoprotein lipase, resulting in a lowering of triglycerides and possibly VLDL; and (2) bile acid sequestrants, better known as resins, cholestyramine and colestipol, which binds and removes bile acids in the intestines. The liver requires cholesterol to make more bile acids and therefore removes LDL from the blood for this function. Fibrates and resins have not found widespread use because the former is associated with hepatitis and a two-fold increased risk of gallstones and the later is associated with gastrointestinal discomfort and an increase in triglycerides, another CHD risk factor. An analysis of several studies even showed a slight increase in overall deaths due to the use of fibrates.

An additional approach to preventing CVD is the reduction of blood triglyceride level. Most fats eaten in food or converted from carbohydrates exist in the form of triglycerides. Hypertriglyceridemia, i.e., elevated blood triglyceride level, is a well known risk factor for coronary heart disease. The fibrates described above are the most effective drug for lowering triglyceride level but is only moderately effective for lowering LDL. Combination drug therapy has thus become more popular in recent years.

It has now been generally accepted that LDL cholesterol becomes harmful only in its oxidized form. Native LDL consists of phospholipids, triglycerides, cholesterol, both free and as an ester, fatty acids (50% of which is polyunsaturated), proteins and lipophilic antioxidants that protect the polyunsaturated fatty acids (PUFA) in cholesterol against free radical attack and oxidation. The first step in the oxidation of cholesterol is the production of free radicals, which are generally induced by oxidative stress. These radicals act to deplete lipids of their natural antioxidants, such as vitamin E and carotinoids, and are also highly reactive against proteins, DNA, PUFA and lipids. Once the natural antioxidants are depleted, the free radicals move to oxidize unprotected LDL. The oxidized cholesterol molecule is recognized by scavenger receptors and internalized by macrophages in the form of lipid loaden foam cells, the first step in the formation of atherosclerotic plaque. Oxidative stress may occur when formation of reactive oxygen species increases, scavenging of reactive oxygen species or repair of oxidatively damaged macromolecules decreases, or both. Thus, factors such as exposure to environmental pollutants and pesticides can instigate the generation of oxysterols internally.

Nutritional aspects of atherosclerosis include the role of antioxidants in the diet such as beta-carotene, selenium, vitamin E, and vitamin C. Fats and cholesterol are very susceptible to free-radical damage and form lipid peroxides as well as oxidized cholesterol when exposed to free radicals. These products of free-radical damage impair artery walls and accelerate the progression of atherosclerosis.

Vitamin E has been studied in depth for its effects on cardiovascular disease. For example, studies have shown that supplementation with just 30 IU to 100 IU of vitamin E results in patients having a 41% lower risk of heart disease. Another study showed that supplementation with 100 IU of vitamin E results in reduced progression of coronary artery disease. Despite these earlier promising results, more recent findings suggest that vitamin E has no effect on foam cell production, although supplementation with vitamin E does indeed increase the levels of vitamin E in cells such as macrophages. The same study concluded that there is a direct correlation-between foam cell production and depletion of cellular vitamin E, though this does not correlate with the amount of cell lysis by oxidized LDL.

More recent efforts towards anti-atherogenic drugs have been directed at compounds with properties. Amlodipine, a new-calcium antagonist, was determined to normalize elevated levels of oxidized LDL cholesterol without reducing elevated total plasma cholesterol levels. Initial results indicate that atherosclerosis progression was suppressed in monkeys who had been fed an atherogenic diet. Monatepil, an alpha 1-adrenoceptor-blocking drug with antilipid peroxidation activity was also found to reduce plasma lipid levels.

Polyphenols have been associated with beneficial effects in the prevention of atherosclerosis. Many plant phenols and flavonoids contain important dietary antioxidants. It has been speculated that compounds found in red wine or in the Mediterranean diet could explain the "French paradox". This would explain why there is a lower mortality rate due to cardiovascular disease in France and Mediterranean countries, as compared to the other developed countries such as the United States, though the French diet is high in polysaturated fats. Substituted phenols and thiophenols have been documented as antioxidant chemicals for inhibiting the peroxidation of LDL cholesterol as well.

South America offers a wide diversity of plants and unique seasonal crops mainly due to the presence of natural areas such as the Andean mountains or the Amazon rainforest. Several scientific reports have pointed out the therapeutic potential of certain food plants from Andean mountains such as "maca" (*Lepidium meyenii*) and "yacon" (*Smallantus sonchifolius*) that have been linked to multipharmacological properties. *Cyclanthera pedata* Schrad is of South American origin, where it is known by the common name of "achojcha", "achocha", "caygua", "caihua", "achuqcha" (quechua name). It is thought to be native to the Andean region or "Sierra", and was cultivated by the Incas who used its fruits as food. The fruit is a berry (10-20 cm length) with irregular surface, soft spines and longitudinal grooves. Its color varies from dark green to white. The mesocarp (edible part) is thin and succulent. The endocarp is white and fluffy. Its seeds are roughly quadrangular and rough black. Actually, the "achojcha" fruits are largely used in South America to make salad or soup for their medicinal properties popularly attributed, such as anti-inflammatory, hypoglycemic and hypocholesterolemic. It thus represents an example of a plant used for medicinal purposes, and can appropriately be considered within the above-described context of food plant with health-giving effects. For this reason, *C. pedata* has a commercial interest in the functional food market. The nations involved in promoting the diffusion of this species are Peru, Ecuador (in particular the southern part), Bolivia, Colombia, Venezuela and north of Argentina. Fruits and seeds are rich in cucurbitacins, which are important as chemotaxonomic markers. A number of studies have highlighted the presence of saponins in fruits and seeds and O and C-glycosides of chrysin and apigenin in fruits. It was recently described inhibitory activity of angiotensin I-converting enzyme (ACE).

*Cyclanthera pedata* (also known as Caigua, "cucumber filling", "Suñez", Achogcha, Peruvian Maxixe and many other names as further shown below) is a slender tropical vine that is indigenous to South America. It grows up to 40 feet in length with long tendrils for climbing. The leaves are 4-5 inches wide and divided into several lobes. It produces a pale green, semi-flattened fruit resembling a cucumber that is 4-6 inches long and 2-3 inches wide. Unlike a cucumber, the inside of the ripe fruit is hollow (much like a bell-pepper), with several black seeds attached to a placenta. In South America the fruits are eaten much like bell peppers—either raw or cooked (after the seeds are removed). They are also prepared as stuffed peppers; stuffed with meat, fish or cheese and then baked—earning its name "stuffing cucumber." Caigua is currently cultivated as a food in the Caribbean, Central and South America. It has been introduced into Florida where it is called "wild cucumber" and is considered a weed pest in lawns and gardens.

Domesticated in the Andes and traditionally distributed from Colombia to Bolivia, the caigua is now grown in many parts of Central America and also in parts of the Eastern Hemisphere tropics. For example, caiguas are very popular in northeastern India, Nepal and Bhutan. The Moche culture had a fascination with agriculture and displayed this in their art. Caiguas were often depicted in their ceramics. Typically, the immature fruits are eaten cooked, raw in salads, and pickled. The caigua has a subtle flavour similar to other edible cucurbit fruits. The fruit has a large cavity in which the seeds develop, and this can be filled with other foods to make caigua dishes. This may have inspired the local Andean name pepino de rellenar ("stuffing cucumber"). The young shoots and leaves may also be eaten as greens.

There are about 30 species of *Cyclanthera* that are native to warm-temperate and tropical America. Caigua can stand more cold than many others and it can be found growing prolifically in mountainous valleys in South America up to 3,000 m in elevation. The plant is known in Peru by its Spanish name caigua or caihua. Its indigenous Quechua name is achocha or achoccha. Achocha is a plant of the tropics, where it can be found at elevations up to 3,000 meters. It can also be cultivated in the subtropics and in areas of the temperate zone that have a long, warm growing season of 4 months or more. Requires a very warm, sunny and sheltered position in a rich well-drained soil. The plant is considered to be a weed pest in Florida. The first harvest of fruit can take place about 3 months after planting, and can then continue for several months.

In herbal medicine systems in Peru, a tea from the fruit seeds is used for controlling high blood pressure. The seeds are also dried and crushed and taken in 1 gram doses for intestinal parasites. The seeds and/or the fruits are also recommended for gastrointestinal disorders. The leaves of caigua are considered hypoglycemic and prepared in a decoction for diabetes. The fruits are boiled in milk and gargled for tonsillitis. The fruit juice is also recommended for high cholesterol, hypertension, tonsillitis, arteriosclerosis, circulatory problems, diabetes and as a diuretic. The fruit and/or the leaves are boiled in olive oil and used externally as a topical anti-inflammatory and analgesic. The roots are used to clean the teeth.

It is also known that caigua seeds contain 28-30 amino acids as well as a group of trypsin inhibitors. The leaves of the plant were recently reported to contain two new malonyl derivatives. The fruits are known to contain flavonoid glycosides including four novel ones never reported before that have shown an antioxidant effect in laboratory research. In addition, the fruits have yielded nine triterpenoid saponins, among them six new natural compounds never seen before. The seeds have been reported with six new cucurbitacin glycosides Plant chemicals reported in caigua fruit include phenols, peptin, galacturonic acid, picrin, lipoproteins, flavonoids, glycosides, mucilage, alkaloids, lipids, tannins, terpenes, resins, carbohydrates, sterols, scoparin, vitamins, vitexin, and minerals.

Research conducted in Peru has reported that caigua can lower cholesterol levels in humans. A double-blind placebo study with 60 patients over one year reported that 82% of the patients lowered their total cholesterol by an average of 18.3% by reducing LDL by 23% and raising HDL-levels by 42%. Patients were given either a placebo, 2 or 4 or 6 300 mg capsules daily of dehydrated fruit juice. Another study with 29 patients reported similar results in 10 days with total cholesterol dropping by 21.1% (LDL decreased by 63.55% and triglycerides by 36.37%). These subjects were given 100 cc daily of fruit juice (the equivalent of about 6 fresh fruits). Another study with 17 patients reported an average drop in cholesterol of 21.51% after 21 days taking two (300 mg dehydrated fruit juice) capsules daily (LDL decreased by 22.57% and triglycerides by 16.33%). In a 12-week study with postmenopausal women taking 6 (300 mg) capsules of caigua dehydrated fruit juice, they reported women lowered LDL cholesterol by 33% and increased HDL by 33%. There were no drug interactions, contraindications or side effects reported in any of the studies.

Caigua products have been gaining in popularity and availability in the U.S. natural products market over the last several years. Most are marketing these supplements as a cholesterol management aid, for hypertension, and blood-sugar regulation. Most of the available products in the United States are tablets or capsules of the dried or freeze-dried fruit juice.

BRIEF DESCRIPTION OF THE FIGURES

FIG. 5 is a graphical representation of the levels of serum oxidized LDL cholesterol at each of the study periods (baseline, 45 days and 90 days) and for each of the groups (dose of 2 softgels and dose of 4 softgels). * $p<0.05$.

OBJECTS OF THE INVENTION

Figure 1:
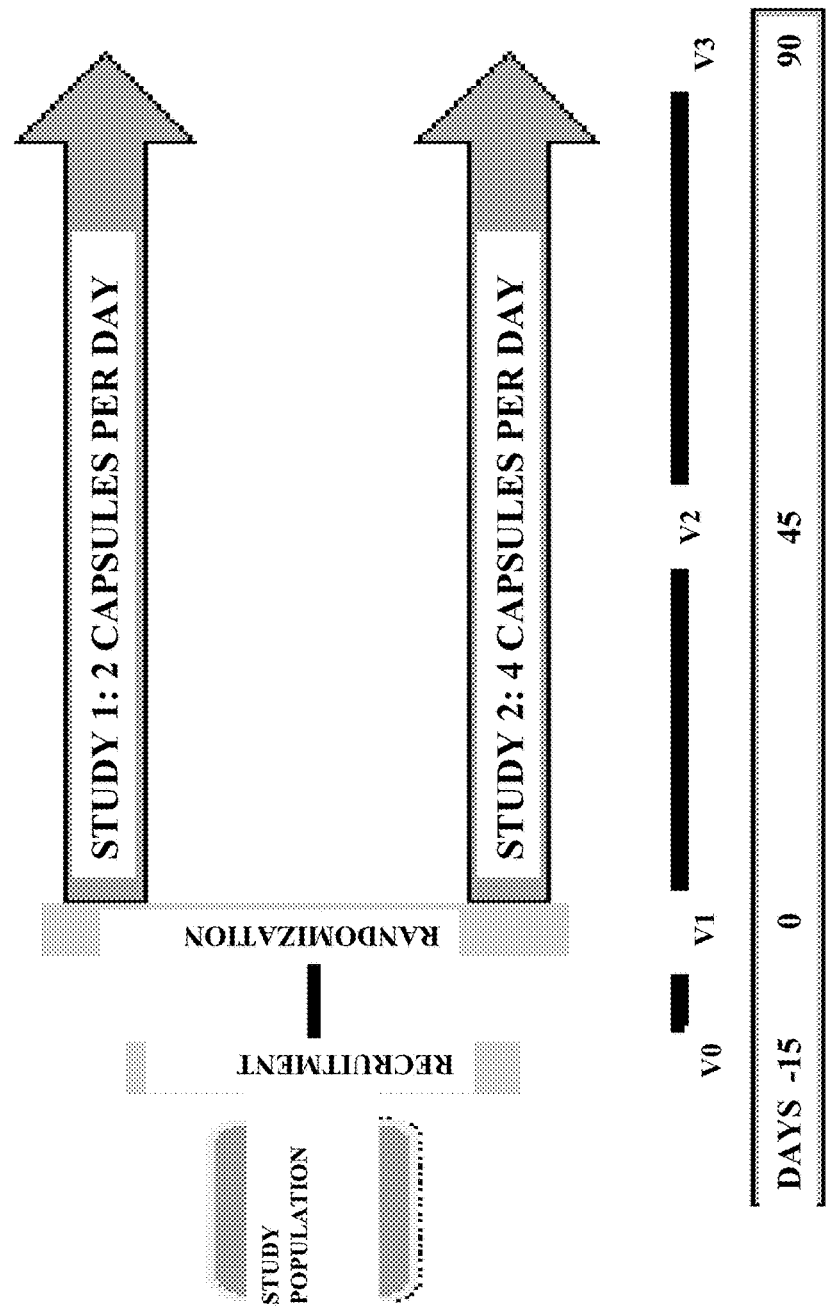
FIG. 1 is a schematic of the clinical study design.

It is an object of the present invention to provide a method for decreasing one or more blood cholesterol levels in individuals.

It is a further object of the present invention to provide an extract capable of reducing total body fat percentage, increasing lean muscle mass, and/or decreasing blood cholesterol levels in individuals.

It is a further object of the present invention to provide a method for decreasing total body fat percentage, increasing lean muscle mass and/or decreasing blood cholesterol levels without the dangerous side effects of other drugs.

It is another object of the present invention to provide a method of extracting active materials from *Cyclanthera pedata* and other solid-form extract that may be used to decrease body fat percentage, increase lean muscle mass and/or decrease blood cholesterol levels in individuals.

It is another object of the present invention to provide a method for decreasing total body fat percentage, increasing lean muscle mass and/or decreasing one or more blood cholesterol levels by treatment with *Cyclanthera pedata* solid-form extract, in an easily ingestible form such as in capsule form.

It is yet another object of the present invention to provide pharmaceutical compositions, preferably in unit dosage form, comprising an extract of *Cyclanthera pedata* and, especially, a solid-form extract of *Cyclanthera pedata*.

These and other objects are readily achieved by providing a method of preparing an easily ingested extract of *Cyclanthera pedata* and related pharmaceutical compositions which, when taken regularly, have the effect of decreasing body fat percentage, increasing lean muscle mass and/or decreasing blood cholesterol levels.

SUMMARY OF THE INVENTION

The invention provides a composition capable of inhibiting cholesterol biosynthesis which is preferably obtained from whole plants or from one or more parts thereof, for example stems, stalks, roots, shoots, rhizomes, tubers, fruits, foliage, kernels, husks, hulls or mixtures thereof, Preferably, the composition is an extract from whole plants or plant parts. Such extracts can be obtained by harvesting the plants, optionally comminuting the plants and/or separating certain parts of the plants, drying, extracting the plants or plant parts using liquid extraction, and optionally concentrating the extract. Drying of the plants is usually necessary to avoid degradation of labile components or microbial contamination upon storage, transport or processing, and results in lowering the water content from e.g. 50-95% to e.g. less than 25%, preferably less than 20%, most preferably between 5 and 15%. Drying is performed under mild conditions i.e. at temperatures between 0° and 80° C., in particular between 10° and 60° C., or by freeze-drying. Before or after drying, the plants or plant parts may be reduced in particle size to coarse fragments or even to fine powder by processes such as grinding, flaking or mincing. Grinding using a hammer mill or equivalent machine is preferred. Extraction according to the invention refers to separating the desired plant material by physical or chemical means, preferably with the aid of a solvent. Suitable solvents include water, water-alcohol mixtures, alcohols, ethers, hydrocarbons or other organic solvents or mixtures thereof Water and water-based solvent mixtures are preferred. Extraction can be performed by maceration, i.e. soaking for a time between e.g. one minute and several hours, optionally using agitation, followed by filtration. Percolation may also be used for the extraction process as further illustrated below. For larger scale operations, counter-current extraction can be used. The resulting solutions can be concentrated to liquid or solid extracts using e.g. tin layer evaporators, freeze-drying or spray-drying techniques. Spray-drying resulting in concentrated to dry powders is preferred. Suitable plant extracts containing inhibitors of cholesterol biosynthesis are commercially available.

The present invention also provides a method for extracting active therapeutic components from plant materials of the *Cyclanthera pedata* plant which comprises immersing said plant material containing active components and selected from the group consisting of fruits, flowers, leaves, stems, twigs, bark, wood, buds, seeds, roots, and pods in a solvent including water, water-alcohol mixtures, alcohols, ethers, hydrocarbons or other organic solvents or mixtures for a period of time of about 30 minutes to about 15 days to achieve transfer of active components from the plant material to the solvent, separating the solvent containing active components from the plant material, and evaporating or distilling the solvent to produce a concentrated fraction containing active components.

The invention provides a solid-form extract derived from the fruit of *Cyclanthera pedata* plants produced by a process comprising the following steps: (1) immersing the fresh fruit from said plant in an aqueous solution, solution containing an organic peracid for a period of time of about 2 minutes to 2 hours, (2) cutting the fruit into strips and removing the seeds and mucilage form said strips, (3) drying said strips at a temperature between 10° C. and 80° C.; (4) milling said strips to produce a powder having a size of about 1 nm to about 10 mm; (5) Obtaining a concentrated liquid extract by immersing the milled material in a polar solvent including water, water-alcohol mixtures, alcohols, ethers, hydrocarbons or other organic solvents or mixtures thereof for a period of time of about 30 minutes to 15 days and perform an extraction process based on one or a combination of the following procedures: maceration, percolation, soxhlet extraction, microwave assisted extraction, ultrasound assisted extraction, accelerated solvent extraction, enhanced solvent extraction, pulse electric field assisted extraction and steam distillation; (6) concentrating said liquid extracts between 20 to 80% solids (7) absorbing said extract in a carrier and dry the concentrate liquid extract using conventional air drying methods or oven method or flash drying method or steam drying or fluid bed or spray drying or vacuum or radiation drying method to yield a solid-form extract of *Cyclanthera pedata*.

The instant invention further provides a pharmaceutical composition comprising, in combination with a pharmaceutically acceptable carrier, an extract derived from the fruit of *Cyclanthera pedata* plants produced by the steps of: (1) immersing the fresh fruit from said plant in an aqueous solution, solution containing an organic peracid for a period of time of about 2 minutes to 10 minutes, (2) cutting the fruit into strips and removing the seeds and mucilage form said strips, (3) drying said strips at a temperature between 10° C. and 80° C.; (4) milling said strips to produce a powder having a size of about 1 nm to about 2-10 mm; (5) Obtaining a concentrated liquid extract by immersing the milled material in a polar solvent including water, water-alcohol mixtures, alcohols, ethers, hydrocarbons or other organic solvents or mixtures thereof for a period of time of about 30 minutes to 15 days and perform an extraction process based on one or a combination of the following procedures: maceration, percolation, soxhlet extraction, microwave assisted extraction, ultrasound assisted extraction, accelerated solvent extraction, enhanced solvent extraction, pulse electric field assisted extraction and steam distillation; (6) concentrating said liquid extracts between 20 to 80% solids (7) absorbing said extract in a carrier and dry the concentrate liquid extract using conventional air drying methods or oven method or flash drying method or steam drying or fluid bed or spray drying or vacuum or radiation drying method to yield a solid-form extract of *Cyclanthera pedata*.

The invention also features a pharmaceutical composition for oral ingestion comprising a measured portion of an extract of *Cyclanthera pedata* and a pharmaceutically acceptable carrier.

The invention is also a method of lowering the cholesterol level of a mammalian subject comprising administering to the subject a repeated series of doses of the solid-form *Cyclanthera pedata* extract produced as shown above.

The present invention also provides a kit for use in decreasing body fat percentage, increasing lean muscle mass or lowering the cholesterol level of a mammalian subject, comprising (1) a measured portion of a solid-form *Cyclanthera pedata* extract and (2) instructions directing the ingestion by the subject of said extract in a repeated series of doses over a period of time sufficient to decrease body fat, increase muscle mass or lower cholesterol levels.

The instant invention is also directed to an extract derived from the fruit of *Cyclanthera pedata* plants produced by a process comprising the following steps: (1) immersing the fresh fruit from said plant in an aqueous solution, solution containing an organic peracid for a period of time of about 2 minutes to 10 minutes, (2) cutting the fruit into strips and removing the seeds and mucilage form said strips, (3) drying said strips at a temperature between 10° C. and 80° C.; (4) milling said strips to produce a powder having a size of about 1 nm to about 2-10 mm; (5) Obtaining a concentrated liquid extract by immersing the milled material in a polar solvent including water, water-alcohol mixtures, alcohols, ethers, hydrocarbons or other organic solvents or mixtures thereof for a period of time of about 30 minutes to 15 days and perform an extraction process based on one or a combination of the following procedures: maceration, percolation, soxhlet extraction, microwave assisted extraction, ultrasound assisted extraction, accelerated solvent extraction, enhanced solvent extraction, pulse electric field assisted extraction and steam distillation; (6) concentrating said liquid extracts between 20 to 80% solids (7) absorbing said extract in a carrier and dry the concentrate liquid extract using conventional air drying methods or oven method or flash drying method or steam drying or fluid bed or spray drying or vacuum or radiation drying method to yield a solid-form extract of *Cyclanthera pedata*.

The invention further provides a method for decreasing the serum cholesterol of patients with hypercholesterolemia without other pharmacological intervention by administering effective amounts of *Cyclanthera pedata* for at least 90 days. This effect was observed starting after 45 days of consumption. A greater decrease was observed when the subjects consume 2 g of this extract than when they consume 1.

Additionally, the invention provides methods for decreasing serum LDL cholesterol levels as well as serum oxidized LDL cholesterol in patients with hypercholesterolemia without other pharmacological intervention by administering effective amounts of *Cyclanthera pedata* for at least 90 days. This effect was observed starting after 45 days of consumption. Also, a greater decrease was observed when the subjects consume 2 g of this extract than when they consume 1 g.

The invention also provides methods for lowering serum triglyceride levels in patients with hypercholesterolemia without other pharmacological intervention when they consume a *Cyclanthera pedata* extract for 90 days.

The invention also provides that the consumption of an extract of *Cyclanthera pedata* for 90 days is safe on subjects undergoing treatment.

DETAILED DESCRIPTION OF THE INVENTION

As used herein, "extracting" or "extraction" of a solid or liquid material means contacting the material, which if solid is preferably dried and crushed or ground, with an appropriate solvent to remove the substance(s) desired to be extracted from the material. Such an extraction may be carried out by conventional means; for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

"Treatment" covers any treatment of the disease in a mammal, particularly human, and includes: (i) preventing the disease from occurring in a subject which may be predisposed to the disease but has not yet been diagnosed as having it; (ii) inhibiting the disease, i.e. arresting the development of said disease; or (iii) relieving the disease, i.e. causing regression of the disease.

"Hypercholesterolemia" also known as hypercholesteremia or hypercholesterinemia, means the presence of an abnormally large amount of cholesterol in the cells and plasma of the circulating blood.

"Arteriosclerosis" as used herein means a degenerative arterial sclerosis marked by hardening and thickening of the vessel walls.

As used herein, "an effective amount" of a composition is that amount that, when administered to a subject, results in a decrease in cellular cholesterol and cholesteryl ester concentration. As used herein, "a safe and effective amount" of a composition is that amount which is pharmaceutically safe to a subject and that causes a decrease in cellular cholesterol and cholesteryl ester concentration while causing no side effects or an acceptable level of side effects.

The present invention provides an extract of the plant *Cyclanthera pedata* having therapeutic activity against hypercholesterolemia, the method for obtaining the extract, and their use in the treatment of hypercholesterolemia.

The extract of the invention is obtained from the plant of the genus *Cyclanthera* particularly *Cyclanthera pedata* species (synonym *Momordica pedata* L.) belonging to the family Cucurbitaceae. This family includes 118 genera and 825 species characterized as creeping or climbing plants. The *Cyclanthera* is a purely Latin American genus with 31 species, whose flowers are very small. In America there are at least three species of food interest *Cyclanthera: Cyclanthera pedata, Cyclanthera brachybotrys, Cyclanthera brachystachya (Cyclanthera explodens)* the first being chosen because of its performance in production and possibly possessing greater commercial value.

In Colombia it is known as "cucumber filling" in Peru is known as "caigua" in Venezuela as "Suñez" or "cucumber filling", in Ecuador as Achogcha (Quechua name), Kaikua (Aguaruna). In Brazil it is known as Peruvian Maxixe. Other common names are "achojcha", "achocha", "caygua", "Cachua", "achuqcha". Other authors describe it as: achoca, achocha, achoccha, achogcha, achojcha, achokkcha, achoncha, achoscha, archucha, caigua, caihua, caygua, Cayhua, Cayua, chayotero, Korila, maxixi Peru, Andean cucumber, cucumber eat cucumber filling, stuffing cucumber, hollow cucumber. In India it is known as "Karela Metha" or "Korila". The taxonomic classification of the plant is as follows:

UNITED: Plant
DIVISION: Magnoliophyta
Class: Magnoliopsida
ORDER: Cucurbitales
Family: Cucurbitaceae
Subfamily: Cucurbitoideae
Subtribe: Cyclantherinae
GENRE: *Cyclanthera*
SPECIES: *Pedata*

The *Cyclanthera pedata* is a perennial climbing plant and characterized in that the length of the vine can reach several meters in length. The stem is branched and glabrous. This Cucurbitaceae vegetative organs is glabrous (no hairs or trichomes), where the ends of the young shoots are closed. The tendrils have no or few coils and it has between 2 and 3 branches.

The leaves of the plant are light green on the underside and darker on the top, said leaves being lobed with five pinnatifid segments, oblong shape, jagged edges, and an acuminate apex.

The adult stems and petioles are light green, with five prominent ridges. The tendrils have between 2 and 3 branches. The leaves are dark green on the top and light green on the underside. The male flowers are staminate and are found in groups of 10-20 that grow on long pedicels. These appear between 15 to 30 days of seedling emergence. More late female flowers appear at the ends of the branch. The female flowers are found in smaller numbers than the male.

The root is shallow and extensive, considering that in the internodes of the stems and main branches are generally formed two more roots that support.

The fruit, which is the edible part of the plant, is somewhat flattened oblong-elliptical and generally curved pointed apex and about 10-15 cm long and can even reach 20 cm in length and 5-8 cm wide. The fruit has a wide central cavity with placental tissue, and a mesocarp 3-4 mm thick. The endocarp is white and fluffy.

The seeds are square and rough black and they can be a little over 1 cm in size. Planting is by seed at temperatures ranging between 15 and 28° C. and high humidity (80-90%). The vegetative period from planting to harvest lasts for 150 days.

A number of standard extraction techniques known in the art can be employed to prepare the plant extracts. In general, the extraction process entails contacting solid plant material with a solvent with adequate mixing and for a period of time sufficient to ensure adequate exposure of the solid plant material to the solvent such that activity present in the plant material can be taken up by the solvent.

Several approaches can be employed to extract the plant material of the invention. Although water is used as an extractant in many traditional protocols, organic solvents of varying polarities are generally selected in modern methods of extraction to exploit the various solubilities of plant constituents.

Maceration

This simple widely used procedure involves leaving the ground or pulverized plant to soak in a suitable solvent in a closed container. Simple maceration is performed at room temperature by mixing the ground plant material with the solvent (plant material solvent ratio 1:1 or 1:25) and leaving the mixture for several days with occasional shaking or stirring. The extract is then repeated from the plant particles by straining. The process is repeated for once or twice with fresh solvent. Finally the last residue of extract is pressed out of the plant particles using a mechanical press or a centrifuge. Kinetic maceration differs from simple one by continuous stirring.

The maceration method is suitable for both initial and bulk extraction. The main disadvantage of maceration is that the process can be quite time-consuming, taking from a few hours up to several weeks.

Ultrasound-Assisted Solvent Extraction

This is a modified maceration method where the extraction is facilitated by the use of ultrasound. The plant powder is placed in a vial. The vial is placed in an ultrasonic bath, and ultrasound is used to induce a mechanical stress on the cells through the production of cavitations in the sample. The cellular breakdown increases the solubilization of metabolites in the solvent and improves extraction yields. This method is mostly used for the initial extraction of a small amount of material.

Percolation

The ground or powdered plant material is soaked initially in a solvent in a percolator. Additional solvent is then poured on top of the plant material and allowed to percolate slowly (dropwise) out of the bottom of the percolator. Additional filtration of the extract is not required because there is a filter at the outlet of the percolator. The method of percolation is adequate for both initial and large-scale extraction. The main disadvantages are: Fine powders and materials such as resins and plants that swell excessively (e.g., those containing mucilages) can clog the percolator and if the material is not distributed homogenously in the container, the solvent may not reach all areas and the extraction will be incomplete.

Soxhlet Extraction

This method is adequate for both initial and bulk extraction. The plant powder is placed in a cellulose thimble in an extraction chamber, which is placed on top of a collecting flask beneath a reflux condenser. A suitable solvent is added to the flask, and the set up is heated under reflux. When a certain level of condensed solvent has accumulated in the thimble, it is siphoned into the flask beneath. The main advantage of Soxhlet extraction is that it is a continuous process.

Pressurized Solvent Extraction

The powdered or ground plant material is loaded into an extraction cell, which is placed in an oven. The solvent is then pumped from a reservoir to fill the cell, which is heated and pressurized at programmed levels for a set period of time. The cell is flushed with nitrogen gas, and the extract, which is automatically filtered, is collected in a flask. Fresh solvent is used to rinse the cell and to solubilize the remaining components. A final purge with nitrogen gas is performed to dry the material. This method offers a more economical and environment-friendly alternative to conventional approaches.

Extraction Under Reflux and Steam Distillation

Plant material is immersed in a solvent in a round-bottomed flask, which is connected to a condenser. The solvent is heated until it reaches its boiling point. As the vapor is condensed, the solvent is recycled to the flask. This method is commonly applied to the extraction of plant essential oils. The main disadvantage is that thermolabile components risk being degraded.

Extraction with Supercritical Fluids

Supercritical fluids (SCFs) are increasingly replacing organic solvents, e.g., n-hexane, dichloromethane, chloroform, and so on, that are conventionally used in industrial extraction operations because of regulatory and environmental pressures on hydrocarbon and ozone-depleting emissions. Most of the currently available Solvent Free Extraction systems utilize $CO_2$, which is generally considered as safe for solvent-free extraction processes. The fundamental steps involved in SFE are as follows: (1) Liquid $CO_2$ is forced into supercritical state by regulating its temperature and pressure; (2) Supercritical $CO_2$ has solvent power and extracts predominantly lipophilic and volatile compounds; (3) Gaseous $CO_2$ returns to $CO_2$ tank. After a full round, the new extraction starts with circulating $CO_2$.

Countercurrent Extraction

This is a continuous process in which the plant material moves against the solvent. It is suitable procedure for production of large amounts of extracts on an industrial scale. Several types of extractors are available. In the screw extractor the plant material is transported by a screw through a tube and meets the solvent which is pumped in the opposite direction.

The solvents of the invention include water, organic solvents and mixtures thereof. The most preferred solvents are polar solvents and they include aprotic and protic polar solvents. Typical polar aprotic solvents include dichloromethane (DCM), tetrahydrofuran (THF), ethyl acetate, acetone, dimethylformamide (DMF), acetonitrile (MeCN), dimethyl sulfoxide (DMSO) and propylene carbonate. Polar protic solvents include formic acid, n-butanol, isopropanol (IPA), n-propanol, ethanol, methanol, acetic acid, nitromethane and water.

An appropriate amount of the solvent to be used in the extraction can be determined by the skilled worker based on the amount of plant material being employed in the extraction. In one embodiment of the invention, the w/v (g/100 mL) of plant material to solvent used in the extraction process is between about ½ and about 1/50. In another embodiment, the w/v (g/100 mL) of plant material to solvent used in the extraction process is between about ⅕ and about 1/50. In another embodiment, the w/v (g/100 mL) of plant material to solvent used in the extraction process is between about 1/10 and about 1/50. In other embodiments, the w/v (g/100 mL) of plant material to solvent used in the extraction process is between about 1/10 and about 1/40; between about 1/10 and about 1/30; and between about 1/10 and about 1/25.

A variety of conditions can be employed for the extraction process. Typically, the extraction procedures are conducted over a period of time between about 10 minutes and about 15 days at a temperature between about 4° C. and about 50° C. However, temperatures between about 4° C. and about 90° C., for example between about 4° C. and about 70° C. can be employed. Higher temperatures are also contemplated, with or without increased pressure, when certain extraction techniques are employed, for example, pressurised liquid extraction, sub-critical fluid extraction (for example, sub-critical water extraction (SWE)) or supercritical fluid extraction. Similarly, the extraction time may be varied depending on other extraction conditions, such as the solvent and temperature employed, for example, the extraction time can range from several minutes to several days. For example, in one embodiment, the extraction time is at least one hour. In another embodiment, the extraction time is between about one hour and about 72 hours.

Determination of appropriate extraction temperatures and times is within the ordinary skills of a worker in the art.

Adequate contact between the solvent and the plant material can be encouraged by shaking, stirring, percolating and/or macerating the suspension. Alternatively, an extraction device equipped with, for instance, a stirring machine, or a soxhlet or other device known in the art can be employed which may improve the extraction efficiency. The extraction can be carried out at ordinary pressure, under pressure or at reduced pressure established by, for example, aspiration. Appropriate extraction conditions can readily be determined or selected by one skilled in the art taking into consideration the production conditions such as production facilities and yields.

The resulting extract at a given concentration can be absorbed into a solid matrix. The solid matrix is selected from the group consisting of cellulose, microcrystalline cellulose, aerosil, mannitol, starch and other protein or carbohydrate materials suitable for oral administration. In an alternative embodiment, the extract can be dispersed or dissolved with polyethylene glycol and then the resulting formulation can be encapsulated in a softgel capsule. The extract absorbed in a solid matrix can be encapsulated in a hard shell gelatin capsule.

The instant *Cyclanthera pedata* extract can be combined with any pharmaceutically acceptable excipient. According to this invention, a "pharmaceutically acceptable excipient" is an excipient that acts as filler or a combination of fillers used in pharmaceutical compositions. Preferred excipients included in this category are: 1) amino acids, such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-beta-cyclodextrin; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. Salts of such compounds may also be used. By "oral dosage form" is meant to include a unit dosage form prescribed or intended for oral administration. An oral dosage form may or may not comprise a plurality of subunits such as, for example, microcapsules or microtablets, packaged for administration in a single dose. The term "dosage form" denotes a form of a formulation that contains an amount sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics such as solubility, and with the characteristics of the swellable matrix such as its permeability, and the relative amounts of the drug and polymer. The dosage form can be prepared by various conventional mixing, comminution and fabrication techniques readily apparent to those skilled in the chemistry of drug formulations.

Certain oral dosage forms described herein may be "coated". The coating can be a functional or a non-functional coating, or multiple functional and/or non-functional coatings. By "functional coating" is meant to include a coating that modifies the release properties of the total formulation, for example, a sustained-release coating. By "non-functional coating" is meant to include a coating that is not a functional coating. Note that a non-functional coating can have some impact on the release of the active agent due to the initial dissolution, hydration or perforation of the coating but would not be considered to be a significant deviation from the non-coated composition. Enteric coated formulations, which protect the stomach against any irritant effects of the active agent(s), are also possible within the scope of this invention. Such formulations can be coated with a composition that is non-toxic and includes a pharmaceutically acceptable enteric polymer which is predominantly soluble in the intestinal fluid while being substantially insoluble in the low pH of the gastric juices. Examples include polyvinyl acetate phthalate (PVAP), hydroxypropylmethyl-cellulose acetate succinate (HPMCAS), cellulose acetate phthalate (CAP), methacrylic acid copolymer, hydroxy propyl methylcellulose succinate, cellulose acetate succinate, cellulose acetate hexahydrophthalate, hydroxypropyl methylcellulose hexahydrophthalate, hydroxypropyl methylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer (acid number 300 to 330) and also known as EUDRAGIT L, which is an anionic copolymer based on methacrylate and available as a powder (also known as methacrylic acid copolymer, type A NF), methacrylic acid-methyl methacrylate copolymer, ethyl methacrylate-methylmethacrylate-chlorotrimethyl-ammonium ethyl methacrylate copolymer, and the like, and combinations comprising one or more of the foregoing enteric polymers. Other examples include natural resins, such as shellac, and combinations comprising one or more of the foregoing polymers. Yet other examples of enteric polymers include synthetic resin bearing carboxyl groups. The methacrylic acid: acrylic acid ethyl ester 1:1 copolymer solid substance of the acrylic dispersion sold under the trade designation "EUDRAGIT L-100-55" may be suitable.

The *Cyclanthera pedata* extracts and their adsorbates described herein are useful as medicaments or as dietary supplements. Typical formulations contain 0.01 to 99% by weight of the *Cyclanthera pedata* extract.

The extracts or adsorbates can be combined with other beneficial agents for lowering cholesterol or with other agents that provide health benefits. Additional agents include the statins as well as vitamins, minerals, phytosterols, oligo elements, probiotics, prebiotics, fatty acids, flavonoids, polysaccharides, lipoic acid or other plant extracts. Other ingredients that can be combined with the extracts of the invention include oral antihyperlipidemic agents such as ezetimibe and/or nicotinic acid. Combination therapy with one or more of these agents and the *Cyclanthera pedata* extract of our invention is a preferred method of treatment.

The formulations of the invention can also be formulated as a solid capsule within another capsule in the case of incompatibility of components as taught by US published application 2012/0052118 the entire contents of which are incorporated by reference herein.

The invention further provides methods for treating a subject having or at risk of having a hypercholesterolemic condition. In one embodiment, a method for decreasing blood cholesterol or triglycerides in a subject includes administering an amount of an invention composition effective to decrease blood cholesterol or triglycerides in the subject. In another embodiment, a method for inhibiting increases in blood cholesterol or triglycerides in a subject includes administering an amount of an invention composition effective to inhibit increases in blood cholesterol or triglycerides in the subject. In yet another embodiment, a method for improving serum lipid profile in a subject includes administering an amount of an invention composition effective to decrease blood cholesterol or triglycerides in the subject. In still another embodiment, a method for treating a subject having or at risk of having an undesirable or excessive amount of cholesterol includes administering an amount of an invention composition effective to lower cholesterol in the subject.

This invention advantageously permits consumption of the instant *Cyclanthera pedata* extract by a human. In one embodiment, the compositions according to this invention are administered about once a day. In another embodiment, the compositions according to this invention are administered about once a day for a month. In yet another embodiment, the compositions according to this invention are administered for a period longer than a month. It will be appreciated by those of skill in the art that the specific treatment regimen will depend upon factors such as the cholesterol level in the patient, the age and weight of the patient to be treated, the general physical condition of the patient and the judgment of the treating physician.

Applicants' research indicates that the activity of the extract of *Cyclanthera pedata* for reducing LDL cholesterol levels is due to a combination of active ingredients (secondary metabolite) which are particularly present in the fruits of the plant.

The components that have been identified in the fruit of the *Cyclanthera pedata* are: Chrysin-6-C-fucosyl-7-O-glucoside, Chrysin-6C-glucoside, apigenin-6C-fucoside, Chrysin-6-C-fucoside, isovitexin, Chrysin-7-O-hesperidoside, Apigenin-6C malonyl fucoside, Chrysin-6C-fucosyl-7-O-malonyl glucoside and Chrysin-6-C-malonyl fucoside.

Other ingredients in the extracts of *Cyclanthera pedata* include phytosterols, saponins, tannins and anthocyanins.

Other components that have been identified in the extracts include 6-C-glucosyl-luteolin, 6-C-glucosyl-apigenin, 8-C-glucosyl-chrysin, 6-C-(2-acetyl)glucosyl-apigenin, 6-C-(6-malonyl)-glucosyl-apigenin, 8-C-fucosyl-chrysin, 6-C-glucosyl-chrysin, 6-C-(2-fucosyl, 6-malonyl)-glucosyl-chrysin, rhamno(1→6)glucosyl-chrysin, 6-C-fucosyl-apigenin, 8-C-(2-acetyl)glucosyl-chrysin, 6-C-(6-malonyl)glucosyl-chrysin, C-(2-acetyl)fucosyl-apigenin, 6-C-(2-acetyl)glucosyl-chrysin, 6-C-fucosyl-chrysin, 8-C-(2-acetyl)fucosyl-chrysin, C-(acetyl)fucosyl-chrysin isomer and 6-C-(2-acetyl)fucosyl-chrysin.

There have been several clinical studies with ground dried fruit package. One is a single-center, randomized, double-blind Phase II to demonstrate the effectiveness of a presentation caigua dehydrated and encapsulated in 60 subjects between men and women ranging in age between 27 and 63 years of age administered in different doses 2 (600 mg), 3 (900 mg), 4 (1200 mg) and 6 (2400 mg) capsules daily compared to placebo. The treatment was carried out for 12 weeks. The results demonstrate that oral administration of 6 capsules ingested together caigua dehydrated fasting was effective in reducing the levels of total cholesterol, LDL cholesterol and triglycerides and also succeeded in raising HDL cholesterol.

In this study group, 60% of subjects at baseline had higher values of total cholesterol and the end of treatment only 11% had high levels of total cholesterol.

Likewise when we studied postmenopausal women (n=24) and compared to premenopausal women (n=18) shows that the dehydrated and encapsulated in a dose of 6 capsules per day (300 mg/capsule) caigua was able to lower levels of total cholesterol, LDL cholesterol and increase HDL-cholesterol levels (Gonzales et al, 1995). At the end of 12 weeks of treatment, a 33% reduction in LDL-cholesterol levels in postmenopausal women receiving six capsules of caigua observed.

In a single-blind trial in 25 male subjects 40 to 65 years old with hypercholesterolemia were administered daily for 45 days 800, 1200 or 1600 mg of extract caigua in encapsulated form. Each capsule contains 400 mg of extract caigua equivalent to 100 grams of fresh caigua. Subjects received two, three or four capsules and were compared against the control group that received four capsules of placebo. In this study, treatment was done with four capsules prior to eating and the findings indicated significantly reduced initial total cholesterol by an average of 93 mg/dl or 33.8% of initial value. The reduction in LDL cholesterol was 88 mg/dl or 44.5% of the initial value. HDL cholesterol or triglycerides were not modified.

Methods for Treating Hypercholesterolemia

The *Cyclanthera pedata* extract is useful for treatment or prevention of hypercholesterolemia. Accordingly, the invention provides methods for treating or preventing hypercholesterolemia in a subject, comprising administering to a subject in need of such treatment or such prevention an effective amount of *Cyclanthera pedata* extract.

Experiments carried out on hypercholesterolemic rats indicated that the supplementation of the rats' diets with *Cyclanthera pedata* extract resulted in statistically significant reductions in serum levels of total cholesterol and LDL cholesterol, as well as triglycerides, when compared to hypercholesterolemic rats fed normal food without supplementation and when compared to hypercholesterolemic rats fed food supplemented with niacin, a standard cholesterol reducing drug. Unexpectedly, the hypercholesterolemic rats fed *Cyclanthera pedata* extract also experienced an elevation in serum HDL cholesterol levels compared to hypercholesterolemic rats fed normal food without supplementation and hypercholesterolemic rats fed food supplemented with niacin. This experimental data indicates that *Cyclanthera pedata* extract is useful for reducing serum levels of total cholesterol in a subject, reducing serum levels of LDL cholesterol in a subject, reducing serum levels of triglycerides in a subject, and increasing serum levels of HDL cholesterol in a subject.

Supplementation of diet with the *Cyclanthera pedata* extract resulted in greater reduction in total serum cholesterol, serum LDL cholesterol, and serum triglyceride levels, and further resulted in an increase in serum HDL levels.

Methods for Reducing LDL Cholesterol Levels

The *Cyclanthera pedata* extract is useful for reducing LDL cholesterol levels in a subject in need thereof. Accordingly, the invention provides methods for reducing LDL cholesterol levels in a subject, comprising administering to a subject in need of such reduction an effective amount of *Cyclanthera pedata* extract. Experiments carried out on hypercholesterolemic rats indicated that the supplementation of the rats' diets with *Cyclanthera pedata* extract resulted in significant reductions in serum levels of LDL cholesterol compared to hypercholesterolemic rats fed normal food without supplementation and hypercholesterolemic rats fed food supplemented with niacin, a standard cholesterol reducing drug. This experimental data indicates that *Cyclanthera pedata* extract is useful for reducing serum levels of LDL cholesterol in a subject.

Methods for Reducing Triglyceride Levels

The *Cyclanthera pedata* extract is useful for reducing triglyceride levels in a subject in need thereof. Accordingly, the invention provides methods for reducing triglyceride levels in a subject, comprising administering to a subject in need of such reduction an effective amount of *Cyclanthera pedata* extract. Experiments carried out on hypercholesterolemic rats indicated that the supplementation of the rats' diets with *Cyclanthera pedata* extract resulted in significant reductions in serum levels of triglycerides compared to hypercholesterolemic rats fed normal food without supplementation and hypercholesterolemic rats fed food supplemented with niacin, a standard cholesterol reducing drug. This experimental data indicates that *Cyclanthera pedata* extract is useful for reducing serum levels of triglycerides in a subject.

Methods for Increasing HDL Cholesterol Levels

The *Cyclanthera pedata* extract is useful for increasing HDL cholesterol levels in a subject in need thereof. Accordingly, the invention provides methods for increasing HDL cholesterol levels in a subject, comprising administering to a subject in need of such reduction an effective amount of *Cyclanthera pedata* extract. Experiments carried out on hypercholesterolemic rats indicated that the supplementation of the rats' diets with *Cyclanthera pedata* extract resulted in significant increases in serum levels of HDL cholesterol compared to hypercholesterolemic rats fed normal food without supplementation and hypercholesterolemic rats fed food supplemented with niacin, a standard cholesterol reducing drug. This experimental data indicates that *Cyclanthera pedata* extract is useful for reducing serum levels of triglycerides in a subject.

Methods for Administering *Cyclanthera pedata* Extract

The *Cyclanthera pedata* extract can be administered to subjects in a variety of ways. In one embodiment, the *Cyclanthera pedata* extract is administered orally to a subject, e.g., in the form of a tablet. The tablet can comprise *Cyclanthera pedata* extract combined, in appropriate quantities, with a suitable medium to form a tablet. In another embodiment, the *Cyclanthera pedata* extract is administered orally to a subject in the form of a capsule. The capsule can comprise *Cyclanthera pedata* extract encapsulated in a standard ingestible capsule$_{[GDVG1]}$.

The *Cyclanthera pedata* extract can also be incorporated into various foods and beverages, thus forming a nutraceutical. Examples of suitable beverages include, but are not limited to, fruit juices and sodas (e.g., colas). Examples of suitable foods include, but are not limited to, chocolates, snacks, confectionery, pizza, foods made from cereal flour (e.g., breads, cakes, crackers, cookies, biscuits, and noodles), and seasonings and spices used to prepare meat.

The *Cyclanthera pedata* extract can be formulated into pharmaceutical compositions together with a pharmaceutically acceptable carrier or vehicle for oral administration in solid or liquid form, or for intravenous, intramuscular, or subcutaneous administration.

Pharmaceutically acceptable carriers for oral administration include capsules, softgels, tablets, pills, powders, troches, and granules. In the case of solid dosage forms, the pharmaceutically acceptable carrier can comprise at least one inert diluent such as sucrose, lactose or starch. Such pharmaceutically acceptable carriers can also comprise additional substances other than diluents, e.g., lubricating agents such as magnesium stearate. In the case of capsules, tablets, troches and pills, the pharmaceutically acceptable carrier can also comprise buffering agents. Carriers, such as tablets, pills and granules, can be prepared with enteric coatings on the surfaces of the tablets, pills or granules. Alternatively, the enteric coated compounds can be pressed into tablets, pills, or granules.

The pharmaceutically acceptable carriers and compositions of the invention are formulated into unit dosage forms for administration to the patients. The dosage levels of active ingredient (i.e., *Cyclanthera pedata* extract) in the unit dosage may be varied so as to obtain an amount of active ingredient that is effective to achieve a therapeutic effect in accordance with the desired method of administration. The selected dosage level therefore mainly depends upon the nature of the active ingredient, the route of administration, and the desired duration of treatment. If desired, the unit dosage can be such that the daily requirement for the *Cyclanthera pedata* extract product is in one dose, or divided among multiple doses for administration, e.g., two, three, or four times per day.

The amounts of *Cyclanthera pedata* effective to achieve a therapeutic benefit could vary from about 50 mg daily to about 5 grams daily. A preferred amount is 1 gram daily and a most preferred amount is 2 grams daily$_{[GDVG2]}$.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

Example I

Pretreatment of the *Cyclanthera pedata* Fruit Prior to Cutting and Grinding

Whole fresh fruit is taken and immersed in a solution of peracetic acid (1.8 ml per 1 lt of water) for about 5 minutes. This solution cleans and disinfects plant material of pathogens such as viruses and bacteria. Once disinfected, the fruit is cut into strips and seeds and inner mucilage is removed.

Example II

Preparation of *Cyclanthera pedata* Dried Ground Plant Material for Subsequent Extraction Process After cutting, the plant material is transferred to the drying chamber in which drying is performed by a hot air stream at a temperature between 60 and 70° C. until the product reaches a moisture of between 8% and 10%. At this level of moisture, microorganisms do not grow in the plant material and the plant material may be preserved without decomposition.

After the dried fruit has achieved the desired moisture level, it is then milled where it is processed to achieve a particle size between 2 and 3 mm to facilitate the subsequent extraction process.

Example III

Preparation of Powder Extract from *Cyclanthera pedata* by Hydroalcoholic Extraction 1 kg of dried and ground fruit of *Cyclanthera pedata* is taken and placed in a glass percolator. Subsequently, 3 kg of anhydrous ethanol or 96% ethanol as solvent is added and allowed to flow continuously for 8 hours. The ethanol extract was then collected in a distillation flask and the percolator flow is stopped.

An additional 1 kg of 96% ethanol (1:1) is added and static contact is allowed for 12 hours. After the 12 hours have elapsed, allow for continuous flow and then the ethanol extract was collected. The above step is repeated with the addition of 1 kg of solvent. All extracts obtained are mixed, homogenized and concentrated by conventional distillation or fractional distillation up to 40% concentration to obtain a fluid extract mix. Finally, the concentrated extract is absorbed into a microcrystalline cellulose matrix in a 1:1 ratio of extract to matrix.

Example IV

Clinical Study for Treating Hypercholesterolemia

The present clinical exploratory intervention study is a randomized, double-blind, placebo-controlled all in parallel, to assess the health effects and tolerance of an extract of *Cyclanthera pedata* on different indicators of cardiovascular risk parameters and oxidative stress in a sample of patients with hypercholesterolemia The objective of the study is to evaluate the health effects of *Cyclanthera pedata* extract on different indicators of cardiovascular risk parameters and oxidative stress in a sample of patients with hypercholesterolemia The clinical intervention study is of 56 days (8 weeks) in duration and is a randomized in parallel with double-blind and placebo-controlled.

The following are the requirements for the study:
Sample size: Number of clinical trial subjects=60 volunteers (30 men and 30 women).
Participants will be randomized by sex in 4 study arms *Cyclanthera pedata* to consume three doses (n=45) and the "placebo" (n=15). Inclusion/exclusion.
Subjects of both sexes (men or women).
Age between 18 and 65 years inclusive.
Suitable culture and level of understanding of the clinical trial.
BMI between 19 and 30 kg/m2.
Agree to participate voluntarily in the study and give written informed consent.
The subjects have not been treated with lipid-lowering drugs or any other type of treatment for hypercholesterolemia during the 6 weeks prior to baseline.
Present cholesterol levels Total between 200 and 250 mg/dl.
Present levels of LDL-cholesterol of between 130 and 190 mg/dl.
Do not submit triglyceride levels above 350 mg/dl.
not having presented any cardiovascular ischemic event during the last 6 months.
No pregnant or lactating women.
Do not be hypersensitive to any component of the product under study.
Not having participated in another clinical trial in the three months prior to baseline.
Treatment The 60 participating subjects will be randomized according to sex in 4 study arms. 45 people will be administered 3 different dosages of *Cyclanthera pedata* during the experimental therapeutic intervention. Each dose is a capsule containing 473 mg of the extract.

Experimental Treatment

Low dosage (473 mg extract): The patient will take one softgel capsule a day before breakfast Medium dosage (946 mg extract): The patient will take two softgel capsules a day before breakfast High-Dosage (1900 mg extract): The patient will take four softgel capsules a day before breakfast.

Treatment Controls

The 15 placebo subjects received orally 946 mg of inert oil in an inert softgel gelatin capsule a product control. The participants are instructed to maintain their diet and habits of everyday life for 56 days (8 weeks). The randomization is done double blind. To do this, the study products (*Cyclanthera pedata*, Placebo) will be labeled with a letter A or B and only the sponsors of the study know what is A or B.

Selection Phase (Week −1)

Prior to the start of the study subjects will be evaluated on a first visit (Visit 0): A decision will e made whether subjects meet the criteria for inclusion/exclusion in the study by clinical history (physical examination) including clinical chemistry evaluation (blood count, biochemistry, systematic and urine sediment, and complementary tests (ECG).

The subjects are verbally informed in writing of the study and must sign an informed consent. Once found to meet the criteria for inclusion/exclusion, they will be given instructions of feeding frequency of 72 h food intake to fill in the days before the beginning of the activity and therapeutic intervention. A questionnaire will be given for physical activity.

Also, information will be given about conducting blood test and they will be given appointments for their first visit.

Experimental Phase

After selection, volunteers will be randomized to take the A or B and products and made three visits to the clinical trials unit where study is conducted.

V1 (Day 0): They will furnish the products to be taken during the next four weeks counting from the day of the first visit. The following tests will be done:

Medical history and Vital signs.

Full Anthropometry: weight data, height, BMI, waist circumference and BIA (MM %, MG %) will be collected.

Measurement of dilatation of the brachial artery flow-mediated (BAFMD).

Full analytics will be done consisting of:

Blood is collected on fasting subjects to determine: —parameters indicative of oxidative stress: antioxidant capacity of plasma (FRAP), lipid peroxidation (TBARS), oxidized LDL, F2-isoprostanes, selenium, vitamin E, enzyme activity in serum PON-1. Inflammation markers: TNF-alpha, IL 6, PAI, CRP, fibrinogen—Lipid profile (Col-t, LDL, HDL, TG).

Measurements related to glucose metabolism include: glucose, insulin, HOMA index atherogenic markers: eNOS, VCAM-1, homocysteine—CBC and safety markers (transaminases, creatinine, uric acid).

The investigator will review the completion of the complete nutritional survey (food frequency, Regular 3-day food record and complete the information required. The questionnaires will be delivered by the subject after filling them.

Each subject will maintain their diet and habits of everyday life throughout the study. In addition, the material must be completed and delivered in the next consultation. Keep a journal to record the consumption of the product every day and record any symptoms and keep a record of 24 hours and a the frequency of food consumption to fill in the days before the next visit. They will be given an appointment for their next visit.

V2 (Day 28): The subjects will be furnished the products to be taken during the next four weeks counting from the day of the first visit.

The subjects will be examined and evaluated according to: Vital signs and body weight (TA, FC).

Basic anthropometry: data on weight, height, BMI is collected

Measurement of dilatation of the brachial artery flow-mediated (BAFMD).

Blood is collected in fasting state to determine: Parameters indicative of oxidative stress: Selenium, vitamin E inflammation markers: PCR, fibrinógeno-Lipid profile (Col-t, LDL, HDL, TG). Parameters related to glucose metabolism: glucose, insulin, HOMA index CBC and safety markers (transaminases, creatinine, uric acid). The investigator will review the completion of the nutrition survey (food frequency, food record 24 hours and complete the information required. The questionaires will be delivered by the subject after filling it.

They indicate that they must maintain dietary styles of everyday life throughout the study guidelines and they will be given an appointment for the next visit.

V3 (Day 56): Upon completion of the trial period, subjects will return to conduct a review of the participating subjects by Vital signs (TA, FC), Full Anthropometry including weight data, height, BMI, waist circumference and BIA (MM %, MG %) will be collected. Measurement of dilatation of the brachial artery flow-mediated (BAFMD). Full analytics will be collected on blood collects in fasting subjects to determine: parameters indicative of oxidative stress: antioxidant capacity of plasma (FRAP), lipid peroxidation (TBARS), oxidized LDL, F2-isoprostanes, selenium, vitamin E, enzyme activity in serum PON-1 markers inflammation: TNF-alpha, IL 6, PAI, CRP, fibrinogen—Lipid profile (Col-t, LDL, HDL, TG), parameters related to glucose metabolism such as glucose, insulin, HOMA index atherogenic markers: eNOS, VCAM-1, homocysteine—CBC and safety markers (transaminases, creatinine, uric acid). In addition to scheduled visits every two weeks an email is sent to each participant as a reminder of the assigned product consumption. Confirmation of receipt thereof is requested.

Main Variables:

Parameters of blood lipids: cholesterol or total and fractions and triglicerides Parameter indicators of oxidative stress: In blood sample: antioxidant capacity of plasma (FRAP) and lipid peroxidation (TBARS) or LDL oxidation F2-isoprostanos, Selenium, vitamin E. Enzyme activity in serum PON-1. Other Variables:—Inflammation markers: TNF-alpha, IL 6, PAI-1, PCR, fibrinogen, —markers of endothelial function and blood pressure BAFMD, atherogenic markers: eNOS, VCAM-1, Homocisteina. Lipid profile (Col-t, LDL, HDL, TG). Parameters related to glucose metabolism: glucose, insulin, HOMA index parameters of body composition (BMI, WC, MG %), side effects:— Creatinine Transaminase Initial Comparison Between Groups Comparison within each group of the results of the values in the parameters indicative of oxidative stress and cardiovascular risk at the beginning and end of treatment. Comparison between groups of parameters indicative of oxidative stress and cardiovascular risk at the beginning and end of treatment. The description of qualitative data will take the form of absolute frequencies and percentages, and quantitative data through with typical average, median and interquartile range, maximum deviation, minimum. Different statistical tests will be used as the form of distribution of variables, Mann-Whitney U (not normal) and T Student (normal) will be used.

Comparability between groups regarding demographic study, basal and secondary variables. Qualitative data are compared with chi-square test, and quantitative test data using appropriate response to the distribution of the variables. All statistical tests were considered as significant bilateral and values, those $p<0.05$.

Example V

Another Clinical Study Design for Treating Hypercholesterolemia and Results

The study design is an exploratory, randomized study with two parallel groups with different doses of the product and unicentric to evaluate the efficacy, safety and tolerance of extracts of *Cyclanthera pedata* on different parameters associated with cardiovascular risk in a sample of patients with hypercholesterolemia without other pharmacological intervention.

FIG. 1 is a schematic showing the study design and Table 1 shows the details of the study.

TABLE 1

|  | Experiment 1 | Experiment 2 |
| --- | --- | --- |
| COMPOSITION: | Extract of *Cyclanthera pedata* 500 mg | Extract of *Cyclanthera pedata* 500 mg |
| DOSAGE: | 2 softgels per day | 4 softgels per day |
| ADMINISTRATION: | Oral | Oral |
| FORM: | Soft gelatin capsules | Soft gelatin capsules |
| MANUFACTURER: | Naturmega S.A. | Naturmega S.A. |

Product Consumption

Each subject received extract of *Cyclanthera pedata*, depending on the experimental group to which it was assigned randomly. The treatments were soft gelatin capsules that had to be ingested before each meal (lunch, dinner), with water or juice. The duration of treatment was 90 days (12 weeks)

Management and Supply of Treatments

The sponsor of the trial (Naturmega S.A.) was responsible for the supply of *Cyclanthera pedata* extract. The study treatments were delivered by the sponsor to the principal investigator, randomized, prepared and correctly labeled. Precautions were taken to ensure that the storage of the study treatment was correct (the containers were protected from sunlight, kept in a cool, dry place and away from intense odors and their direct contact with the soil was avoided).

Treatments not Allowed

During the period that each of the subjects was ingesting the product under investigation, none of them consumed any drug or product enriched with plant sterols.

Population Under Study

The leader of the study selected 11 subjects who had to meet all the selection criteria. Participants were divided into two parallel study groups, one of which will receive extract of *Cyclanthera pedata* in doses of 1 g, and the other will receive the same extract in doses of 2 g.

Selection Criteria

Inclusion Criteria

Subjects of both sexes between the ages of 18 and 65 inclusive.

Clinical history, physical examination by apparatus and laboratory tests within normality (especially the gastrointestinal tract), without evidence of significant disease, organic or psychiatric.

Adequate cultural level and understanding of clinical study

Body mass index (BMI) between 19 and 30 kg/m2

Present total serum cholesterol values below 250 mg/dL

Present LDL-cholesterol levels between 130 and 190 mg/dl.

In the case of presenting two or more cardiovascular risk factors, LDL-cholesterol levels between 100 and 190 mg/dl.

Exclusion Criteria

Present triglyceride levels above 350 mg/dl.

Have presented any ischemic cardiovascular event in the last 6 months.

Be or have been on treatment with lipid-lowering medications or any type of treatment for hypercholesterolemia during the 4 weeks prior to the start of the study.

Pregnant or lactating women.

Hypersensitivity to any component.

Presence of conditions that may cause secondary hypercholesterolemia, presence of significant organic or psychiatric chronic disease, or inability to participate in the study.

Have participated in the development of another clinical trial during the three months preceding the start of the current trial.

Recruitment

The recruitment of the subjects under study was carried out by the researchers of the UCAM. It was corroborated that the volunteers interested in participating in the present study met the inclusion and exclusion criteria.

Randomization

The study product was only identified as A or B and also carried the patient identification number and protocol code. The principal investigator performed randomization. It was carried out by software (Epidat 4.1). Each subject selected and by strict order of incorporation to the study, was assigned a participant number. This number was associated with one of two study groups. Both the investigators and the participant himself did not know the group to which the subject belonged. Therefore, randomization was performed blindly, so that each of the participants and the researcher were unaware of the product or treatment they had received.

Masking and Blind Techniques

This study is open.

Evaluation Variables

Except for the evaluation of adverse events, the remaining variables were obtained by analysis of the serum extracted by venipuncture of the antecubital vein of the arm after 12 hours of fasting. This determination was performed at baseline, 45 days after the beginning of the intake of the product and at 90 days of intake.

Efficacy Variables

Serum lipid profile.

Serum total cholesterol.

Serum triglycerides.

Serum HDL cholesterol (HDL-c).

Serum LDL cholesterol (LDL-c).

Oxidized LDL cholesterol (LDL-ox). Kit Mercodia Oxidized LDL ELISA (Mercodia AB, Uppsala, Sweden).

Safety Variables.

Basic renal and hepatic biochemistry.

Adverse events.

Development of the Study

Selection Phase

First, the Information Sheet was delivered to the participant subject and Conformity by signing the Informed Consent. Subjects were examined and interviewed at the beginning of the study to collect the data that were recorded in the corresponding individual follow-up sheet of each patient. A clinical and blood analysis was performed to determine total cholesterol, HDL-c, LDL-c, LDL-ox and triglycerides. These analyzes were performed on a 12-hour fasting to check the day of the baseline visit that the participants met the study selection criteria.

After the selection phase, patients who met all the criteria for inclusion and none of the exclusion groups were randomized to one of the treatment groups.

Experimental Phase

The 11 patients were divided into two groups for the experimental phase. All participants in the study had to follow a series of hygienic-dietary recommendations that were provided at the beginning of the study by the Principal Investigator:

Do not start or modify any hormonal treatment during the study if it is not properly justified.

Do not modify during the study your diet and physical exercise pattern that each subject was performing before participating in the study.

Do not significantly change habits regarding coffee or alcohol consumption.

Do not take or follow any treatment that could affect the parameters of the study.

Day 0 (Baseline visit).
Inclusion in the study.

The analytical results were evaluated and the tests that were necessary to corroborate that the subject definitively fulfilled the criteria of inclusion in the study Delivery of treatment for the first part of the study.
Day 45 (intermediate visit)
Analytical. Measurements of total cholesterol, HDL-c, LDL-c, LDL-ox and triglycerides.
Safety Parameters
Verification of compliance with treatment during the first part of the study.
Delivery of treatment for the second part of the study
Day 90 (final visit)
Analytical. Measurements of total cholesterol, HDL-c, LDL-c, LDL-ox and triglycerides.
Safety parameters.
Verification of compliance with treatment during the second part of the study.
Ethical Considerations All persons participating in the trial committed to comply with the Helsinki declaration, as well as all relevant national laws and ICH Guidelines of Good Clinical Practice (BPC).

In accordance with the international ethical guidelines for biomedical research in human beings the present study was submitted for its evaluation to the Ethics Committee of the UCAM and authorized its realization.

All subjects were informed of the characteristics of the study verbally and in writing using the information sheet to the participant subject.

Finally, after being fully informed of the implications and restrictions of the protocol, subjects were asked to give written informed consent, together with the investigator, before starting the study. The information sheet model was attached to the volunteer and the informed consent form. By signing and dating the consent form, the subject stated his/her voluntary participation and intention to comply with the Study Protocol and the Investigator's instructions and to respond to questions arising throughout the Study.

As additional information, volunteers were involved in their participation and were warned of the prohibitions of taking other drugs or drugs without the knowledge of the Principal Investigator. They were also warned of all the tests that were done to them.

Statistical Analysis

Initially a descriptive analysis of the variables was performed. The quantitative variables were evaluated by mean and standard deviation and qualitative variables using a frequency table.

For the comparison between the two groups of variables, ANOVA was performed for repeated measures with two factors under study: an intra-subject factor (time: baseline, 45 days and 90 days) and an inter-subject factor (dose: 2 softgels or 4 softgels). Pairwise comparisons were performed with the Bonferroni test.

In the set of statistical tests, the significance level used was 0.05.

Statistical analyzes were performed with the SPSS v 21.0 program.

Results
Clinical Variables

After the recruitment and selection of the subjects, 11 completed the study (6 subjects in The group of 2 softgels and 5 subjects in the group of 4 softgels). Of these, 6 were men and 5 women. The mean age of the individuals was 40.9±6.6 years (40.0±7.7 years in the 2 Softgels group and 42±5.7 years in the 4 softgels group).

Efficacy Variables
Total Serum Cholesterol

In the group that consumed two softgels, the basal serum cholesterol was 224.8±16.3$_{[GDVG3]}$ mg/dl; At 45 days of consumption, this variable had declined in a statistically significant way to 197.0±26.5 mg/dl (P<0.05), representing a decrease of 12.4%; At 90 days, the value of the variable was 208.2±18.3 mg/dl, which means a non-statistically significant decrease from the initial 7.4%.

In the group that consumed four softgels, the basal serum cholesterol was 226.6±21.8 mg/dl; At 45 days of consumption, this variable had declined in a statistically significant way to 196.2±19.0 mg/dl (P<0.05), representing a decrease of 13.4%; At 90 days, the value of the variable was 184.6±22.0 mg/dl, which represents a statistically significant decrease from the initial one of 18.5% (P<0.009).

When comparing the evolution between the two groups, no statistically significant differences were observed, although we observed a trend towards a greater final decrease after 90 days of consumption of the group consuming 4 softgels (p<0.13). Table 2 below is a summary of the data.

TABLE 2

Descriptive statistics (mean and standard deviation) of serum cholesterol (mg/dl) at each of the time points (baseline, 45 days and 90 days) and for each of the groups of 2 softgels and 4 softgels).

|  | DOSE | Median | Standard Deviation | N |
|---|---|---|---|---|
| CHOLESTEROL BASELINE | 2 softgels | 224.8 | 16.3 | 6 |
|  | 4 softgels | 226.6 | 21.8 | 5 |
|  | Total | 225.6 | 18.0 | 11 |
| CHOLESTEROL 45 Days | 2 softgels | 197.0* | 26.5 | 6 |
|  | 4 softgels | 196.2* | 19.0 | 5 |
|  | Total | 196.6* | 22.2 | 11 |
| CHOLESTEROL 90 Days | 2 softgels | 208.2 | 18.3 | 6 |
|  | 4 softgels | 184.6* | 22.0 | 5 |
|  | Total | 197.5* | 22.6 | 11 |

*p < 0.05 when compared with baseline.

Figure 2:
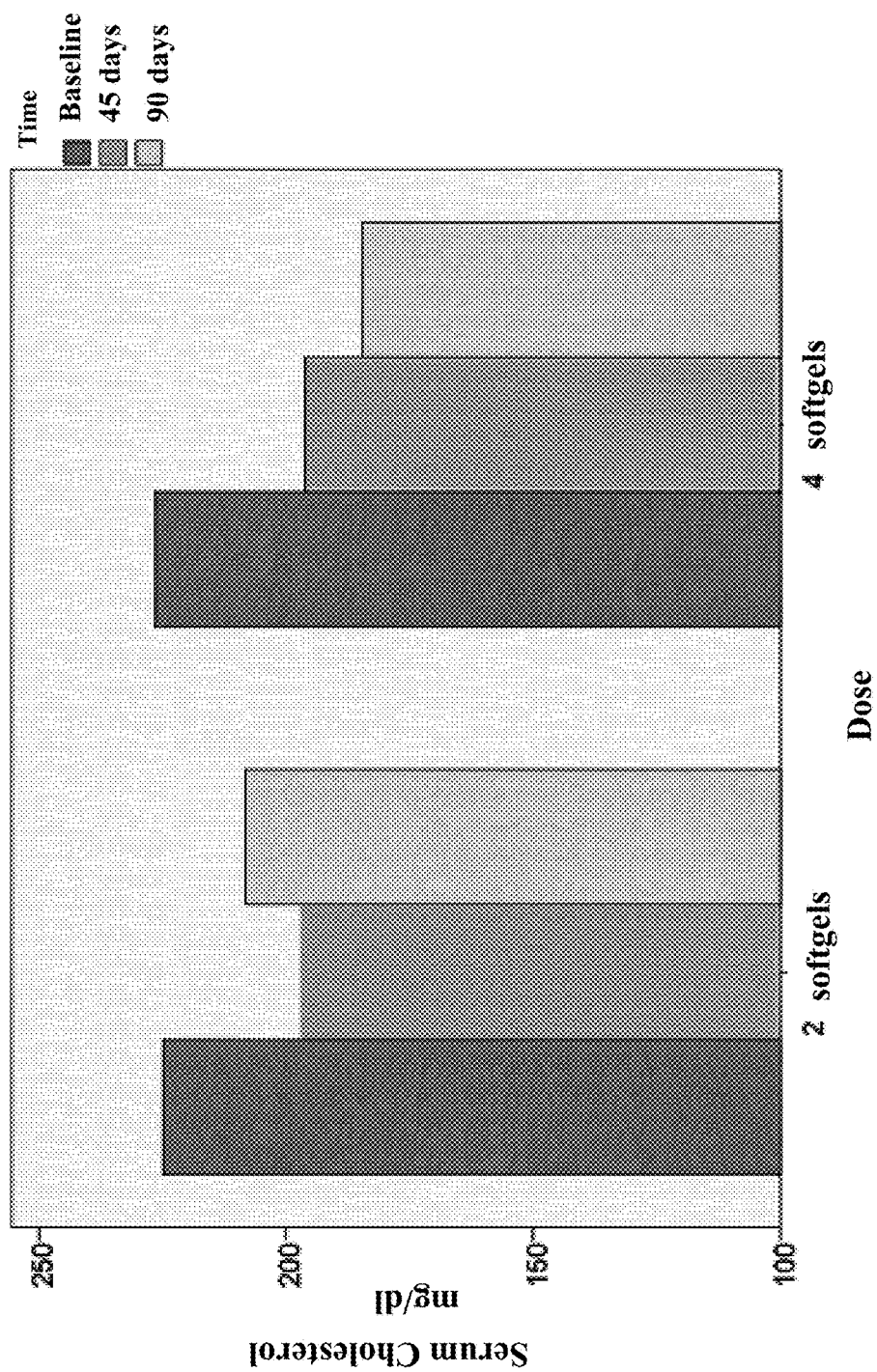
FIG. 2 is a graphical representation of the data of Table 1 for the Serum cholesterol levels at each stage of the study (baseline, 45 days and 90 days) and for each of the groups (dose of 2 softgels and dose of 4 softgels).

FIG. 2 is a graphical representation of the data of Table 2 for the Serum cholesterol levels at each stage of the study (baseline, 45 days and 90 days) and for each of the groups (dose of 2 softgels and dose of 4 softgels). * p<0.05.

Serum Triglycerides

If we considered the sample as a whole (without dividing by dose groups) we noticed a trend towards a decrease in serum triglycerides (p<0.091). Baseline serum triglyceridemia is 104.4±40.4 mg/dl and falls by 45 days to 94.2±30.2 m/dl (9.7%) (p<0.973) and 81.4±23.0 mg/dl at 90 days (22%) (p<0.258).

In the group that consumed two softgels the basal serum triglycerides were 95.7±44.2 mg/dl; At 45 days of consumption, this variable had declined in a statistically insignificant way to 91.8±21.4 mg/dl, representing a decrease of 4.1%; At 90 days, the value of the variable was 72.3±18.5 mg/dl, representing a non-statistically significant decrease from the initial 24.4%. Probably the low sample size has great influence on the lack of statistical significance. In the group that consumed four softgels, basal serum triglycerides were 114.8±37.2 mg/dl; at 45 days of consumption, this variable had declined in a statistically insignificant way to 97.0±41.2 mg/dl, which represents a decrease of 15.5%; at 90 days, the value of the variable was 92.2±25.0 mg/dl, representing a statistically non-significant decrease from the initial 19.6%. Probably the low sample size has great influence on the lack of statistical significance when comparing the evolution between both groups, no statistically significant differences were observed (p<0.705). Table 3 is a summary of the data of the triglyceride measurements.

TABLE 3

Descriptive statistics (mean and standard deviation) of serum triglycerides at each of the time points (baseline, 45 days and 90 days) and for each of the groups (dose of 2 softgels and Dose of 4 softgels).

|  | DOSE | Median | Standard Deviation | N |
|---|---|---|---|---|
| TRIGLYCERIDES BASELINE | 2 | 95.7 | 44.2 | 6 |
|  | 4 softgels | 114.8 | 37.2 | 5 |
|  | Total | 104.4 | 40.4 | 11 |
| TRIGLYCERIDES 45 Days | 2 softgels | 91.8 | 21.4 | 6 |
|  | 4 softgels | 97.0 | 41.2 | 5 |
|  | Total | 94.2 | 30.2 | 11 |
| TRIGLYCERIDES 90 Days | 2 softgels | 72.3 | 18.5 | 6 |
|  | 4 softgels | 92.2 | 25.0 | 5 |
|  | Total | 81.4 | 23.0 | 11 |

Figure 3:
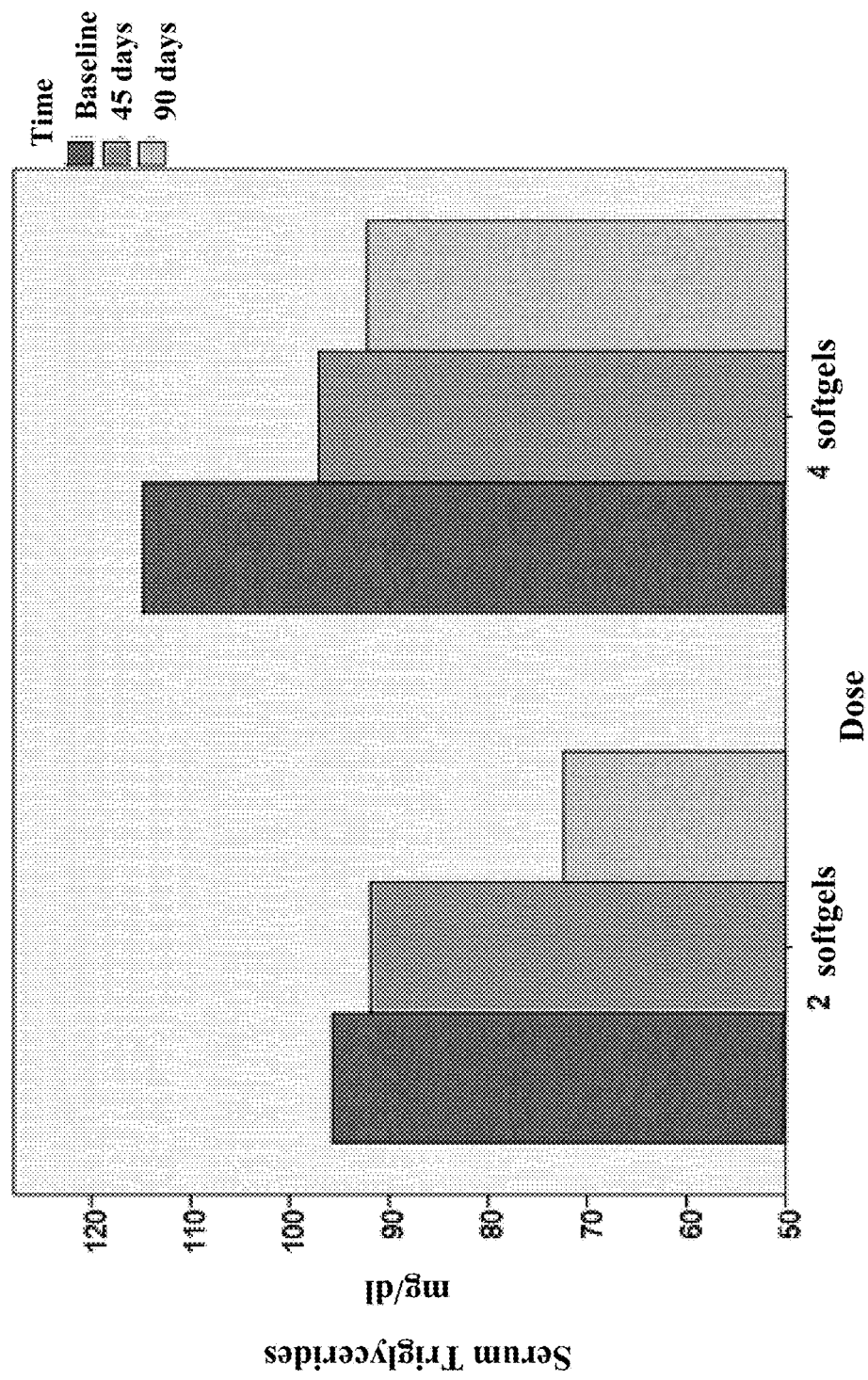
FIG. 3 shows serum triglyceride levels at each of the study periods (baseline, 45 days and 90 days) and for each of the groups (dose of 2 softgels and dose of 4 softgels).

FIG. 3 is a graphical representation of the data on Table 3. FIG. 3 shows Serum triglyceride levels at each of the study periods (baseline, 45 days and 90 days) and for each of the groups (dose of 2 softgels and dose of 4 softgels).

Serum LDL Cholesterol

If we considered the sample as a whole (without dividing by dose groups) we noticed a statistically significant decrease in LDL cholesterol (p<0.002). Baseline serum LDL cholesterol is 142.2±14.0 mg/dl and decreases at 45 days at 116.8±25.6 mg/dl (17.8%) (p<0.006) and at 127.3±22.0 mg/dl at 90 days (10.4%) (p<0.026).

In the group that consumed two softgels, serum LDL cholesterol at baseline was 141.5±10.4 mg/dl; at 45 days of consumption, this variable had declined in a statistically insignificant way to 118.8±30.4 mg/dl (p<0.063), representing a decrease of 16.0%; at 90 days, the value of the variable was 137.5±18.0 mg/dl.

In the group that consumed four softgels, basal serum LDL cholesterol was 143.0±18.7 mg/dl; at 45 days of consumption, this variable had declined statistically to 114.4±21.8 mg/dl (p<0.032), representing a decrease of 20.0%; at 90 days, the value of the variable was 115.0±21.4 mg/dl, which represents a statistically significant decrease from the initial one of 19.6% (p<0.01). When comparing the evolution between both groups, no statistically significant differences were observed, although if we observed a trend towards greater final decrease after 90 days of consumption of the group that consumed 4 softgels (p<0.145). Table 4 below is a summary of the LDL measurements.

TABLE 4

Descriptive statistics (mean and standard deviation) of serum LDL cholesterol at each of the time points (baseline, 45 days and 90 days) and for each of the groups (dose of 2 softgels and Dose of 4 softgels).

|  | DOSE | Median | Standard Deviation | N |
|---|---|---|---|---|
| CHOLESTEROL LDL BASELINE | 2 softgels | 141.5 | 10.4 | 6 |
|  | 4 softgels | 143.0 | 18.7 | 5 |
|  | Total | 142.2 | 14.0 | 11 |
| CHOLESTEROL LDL 45 Days | 2 softgels | 118.8 | 30.4 | 6 |
|  | 4 softgels | 114.4* | 21.8 | 5 |
|  | Total | 116.8* | 25.6 | 11 |
| CHOLESTEROL LDL 90 Days | 2 softgels | 137.5 | 18.0 | 6 |
|  | 4 softgels | 115.0* | 21.4 | 5 |
|  | Total | 127.3* | 22.0 | 11 |

*p < 0.05 when compared with baseline.

Figure 4:
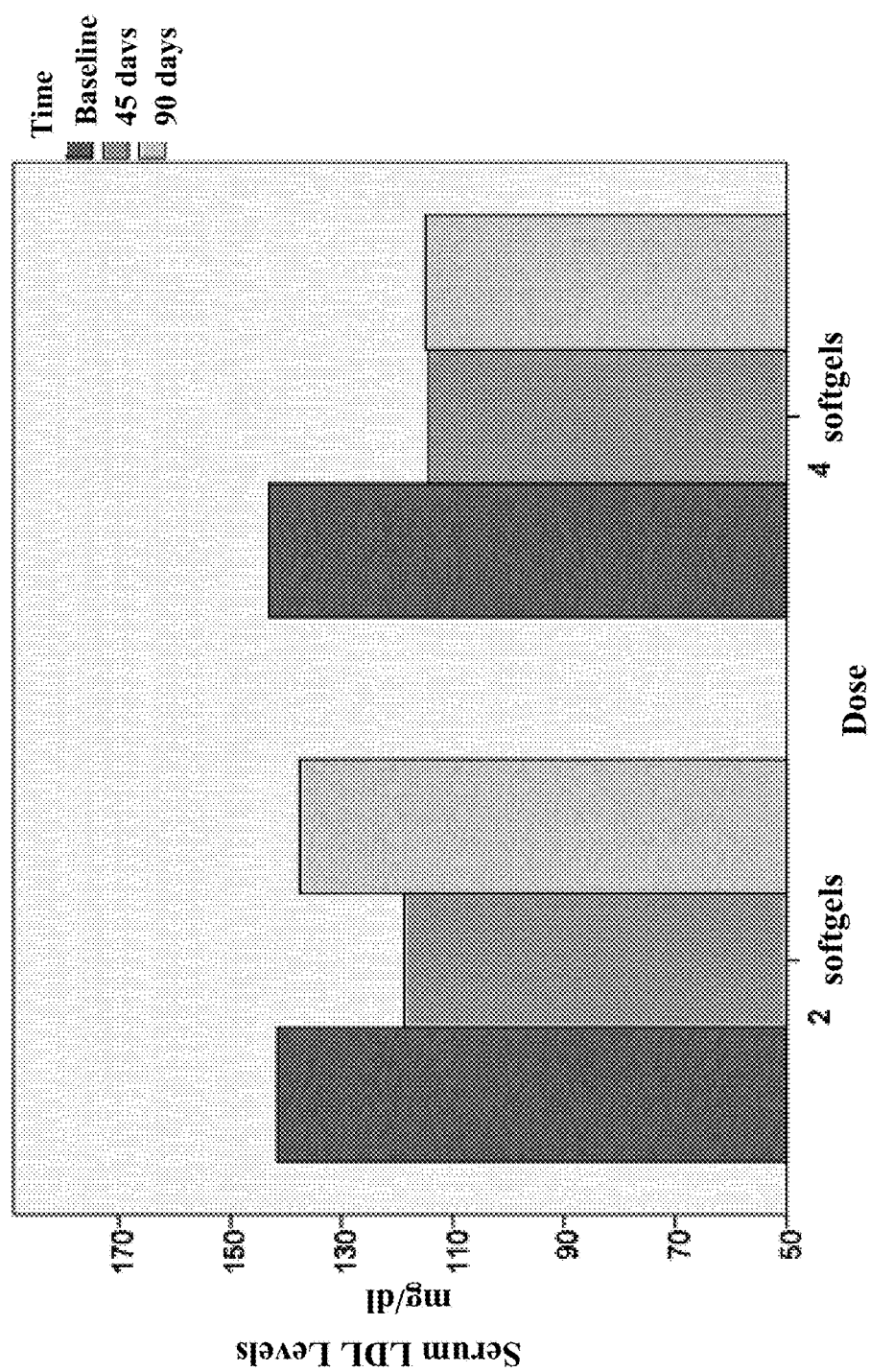
FIG. 4 is a graphical summary of the serum LDL cholesterol levels at each of the study periods (baseline, 45 days and 90 days) and for each of the groups (dose of 2 softgels and dose of 4 softgels).* $p<0.05$.

FIG. 4 is a graphical summary of the serum LDL cholesterol levels at each of the study periods (baseline, 45 days and 90 days) and for each of the groups (dose of 2 tablets and dose of 4 tablets).* p<0.05.

Oxidized LDL Cholesterol

If we considered the sample as a whole (without dividing by dose groups) we noticed a statistically significant decrease in oxidized LDL cholesterol (p<0.001). Baseline serum oxidized LDL cholesterol is 177.7±33.0 IU/L and falls by 45 days to 129.9±20.6 IU/L (26.9%) (p<0.004) and to 100.9±22.0 IU/L at 90 days (43.2%) (p<0.001).

In the group that consumed two softgels, basal serum oxidized LDL cholesterol was 176.2±42.0 IU/L; At 45 days of consumption, this variable had declined statistically to 125.5±26.5 IU/L (p<0.036), representing a decrease of 28.8%; At 90 days, the value of the variable was 96.0±24.0 UI/L, which represents a statistically significant decrease with respect to the initial one 45.5% (p<0.01).

In the group that consumed four softgels, baseline serum cholesterol was 179.5±22.6 IU/L; at 45 days of consumption, this variable had declined statistically to 119.9±12.6 IU/L (p<0.025), representing a decrease of 33.2%; at 90 days, the value of the variable was 106.8±20.3 IU/L, which represents a statistically significant decrease compared to the initial one 40.5% (p<0.02).

When comparing the evolution between both groups, no statistically significant differences were observed (p<0.788). Table 5 below is a summary of the oxidized LDL levels.

TABLE 5

Descriptive statistics (mean and standard deviation) of serum oxidized LDL cholesterol (IU/L) at each of the time points at which the determinations were made (baseline, 45 days and 90 days) and for each of the groups (Dose of 2 softgels and dose of 4 softgels).

|  | DOSE | Median | Standard Deviation | N |
|---|---|---|---|---|
| CHOLESTEROL LDLox BASELINE | 2 softgels | 176.2 | 42.0 | 6 |
|  | 4 softgels | 179.5 | 22.6 | 5 |
|  | Total | 177.7 | 33.0 | 11 |

TABLE 5-continued

Descriptive statistics (mean and standard deviation) of serum oxidized LDL cholesterol (IU/L) at each of the time points at which the determinations were made (baseline, 45 days and 90 days) and for each of the groups (Dose of 2 softgels and dose of 4 softgels).

|  | DOSE | Median | Standard Deviation | N |
|---|---|---|---|---|
| CHOLESTEROL LDLox 45 Days | 2 softgels | 125.5* | 26.5 | 6 |
|  | 4 softgels | 119.9* | 12.6 | 5 |
|  | Total | 122.9* | 20.6 | 11 |
| CHOLESTEROL LDLox 90 Days | 2 softgels | 96.0* | 24.0 | 6 |
|  | 4 softgels | 106.8* | 20.3 | 5 |
|  | Total | 100.9* | 22.0 | 11 |

*$p < 0.05$ when compared with baseline

FIG. 5 is a graphical representation of the levels of serum oxidized LDL cholesterol at each of the study periods (baseline, 45 days and 90 days) and for each of the groups (dose of 2 softgels and dose of 4 softgels). * $p<0.05$.

Safety Variables

Adverse Events

The subjects under study have not described any adverse side effects during the 90-day period of consumption of the product.

Basic Renal and Hepatic Biochemistry

A safety analysis was performed at 45 days of consumption and at 90 days. None of the subjects under study detected a substantial modification of the safety parameters evaluated in the aforementioned times.

TABLE 6

Serum creatinine and urea levels of each of the study subjects at 45 and 90 days of intake of the product.

|  | Creatinine mg/dl | | Urea mg/dl | |
|---|---|---|---|---|
|  | 45 days | 90 days | 45 days | 90 days |
| Natur 01 | 0.99 | 0.97 | 34.2 | 28.1 |
| Natur 02 | 0.85 | 0.8 | 19.9 | 26 |
| Natur 03 | 0.92 | 0.75 | 29.9 | 33.5 |
| Natur 04 | 0.83 | 0.79 | 29.9 | 37.1 |
| Natur 06 | 1.21 | 1.07 | 38.9 | 41.1 |
| Natur 08 | 0.97 | 0.65 | 45.9 | 30.3 |

TABLE 6-continued

Serum creatinine and urea levels of each of the study subjects at 45 and 90 days of intake of the product.

|  | Creatinine mg/dl | | Urea mg/dl | |
|---|---|---|---|---|
|  | 45 days | 90 days | 45 days | 90 days |
| Natur 09 | 0.63 | 0.88 | 43.5 | 28.1 |
| Natur 11 | 0.89 | 0.88 | 32.3 | 43.8 |
| Natur 12 | 0.92 | 0.91 | 31.5 | 25.9 |
| Natur 13 | 0.98 | 0.96 | 41.4 | 45.6 |
| Natur 16 | 1.15 | 0.98 | 51.6 | 36.7 |

TABLE 7

GOT, GPT, GGT and serum bilirubin levels of each of the study subjects at 45 and 90 days of intake of the product.

|  | GOT IU/L | | GPT IU/L | | GGT IU/L | | Bilirrubina mg/dl | |
|---|---|---|---|---|---|---|---|---|
|  | 45 days | 90 days | 45 days | 90 days | 45 days | 90 days | 45 days | 90 days |
| Natur 01 | 21 | 20 | 27 | 22 | 38 | 37 | 0.75 | 0.66 |
| Natur 02 | 20 | 18 | 14 | 12 | 10 | 10 | 0.39 | 0.52 |
| Natur 03 | 15 | 14 | 16 | 21 | 12 | 13 | 0.41 | 0.46 |
| Natur 04 | 18 | 16 | 15 | 13 | 16 | 16 | 0.46 | 0.58 |
| Natur 06 | 12 | 14 | 9 | 14 | 18 | 17 | 0.74 | 0.54 |
| Natur 08 | 13 | 18 | 11 | 14 | 19 | 13 | 0.77 | 0.37 |
| Natur 09 | 20 | 21 | 16 | 25 | 17 | 31 | 0.71 | 0.59 |
| Natur 11 | 18 | 16 | 18 | 14 | 27 | 19 | 1.17 | 0.67 |
| Natur 12 | 25 | 19 | 18 | 17 | 99 | 53 | 1.06 | 0.59 |
| Natur 13 | 17 | 19 | 14 | 21 | 22 | 26 | 0.85 | 0.66 |
| Natur 16 | 20 | 22 | 22 | 31 | 26 | 36 | 1.43 | 1.71 |

The contents of all references cited in the instant specifications and all cited references in each of those references are incorporated in their entirety by reference herein as if those references were denoted in the text.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. A method of lowering serum cholesterol levels in a mammalian subject in need thereof comprising administering to said subject an effective amount of a *Cyclanthera pedata* extract in solid form, wherein the administering is performed in a repeated series of doses, wherein after 45 days of administration, said repeated series of doses leads to a cholesterol reduction of 12.4%, and wherein the extract in solid form is produced by a process comprising the steps of:
   (a) immersing fresh fruit from a *Cyclanthera pedata* plant in an aqueous solution containing peracetic acid for a period of time of about 2 minutes to 10 minutes, (b) cutting the fruit into strips and removing the seeds and mucilage from said strips,
(c) drying the seedless strips at a temperature between 10° C. and 80° C.,
(d) milling the dried strips to produce particles having a size of about 2-10 mm,
(e) extracting the milled particles by immersing them in ethanol and performing an extraction process selected from the group consisting of: maceration, ultrasound-assisted extraction, microwave-assisted extraction, percolation, Soxhlet extraction, pressurized solvent extraction, extraction under reflux, countercurrent extraction and steam distillation, for a period of time of about 30 minutes to about 15 days to obtain a liquid extract,
(f) concentrating the liquid extract from step (e) to between 20% to 80% solids, and
(g) absorbing the concentrated extract in a microcrystalline cellulose matrix in a 1:1 ratio of extract to matrix to yield the *Cyclanthera pedata* in solid form.

\* \* \* \* \*